US007118883B2

(12) United States Patent
Inoue et al.

(10) Patent No.: US 7,118,883 B2
(45) Date of Patent: Oct. 10, 2006

(54) PROCESS FOR PRODUCING PEPTIDES BY USING IN VITRO TRANSCRIPTION/TRANSLATION SYSTEM

(75) Inventors: Akio Inoue, Saitama (JP); Yoshihiro Shimizu, Tokyo (JP); Takuya Ueda, Chiba (JP)

(73) Assignee: Post Genome Institute Co., Ltd., Tokyo (JP)

( * ) Notice: Subject to any disclaimer, the term of this patent is extended or adjusted under 35 U.S.C. 154(b) by 612 days.

(21) Appl. No.: 09/983,067

(22) Filed: Oct. 23, 2001

(65) Prior Publication Data

US 2002/0123101 A1 Sep. 5, 2002

(30) Foreign Application Priority Data

| Dec. 28, 2000 | (JP) | ............................. | 2000-401417 |
| Jan. 15, 2001 | (JP) | ............................. | 2001-006910 |
| Jul. 27, 2001 | (JP) | ............................. | 2001-227094 |
| Sep. 26, 2001 | (JP) | ............................. | 2001-294795 |

(51) Int. Cl.
*C12P 21/06* (2006.01)

(52) U.S. Cl. .................................... 435/68.1; 435/69.1

(58) Field of Classification Search ............... 435/68.1, 435/69.1
See application file for complete search history.

(56) References Cited

U.S. PATENT DOCUMENTS

| 4,683,195 A | 7/1987 | Mullis et al. | |
| 4,710,464 A | 12/1987 | Belagaje et al. | |
| 5,478,730 A | 12/1995 | Alakhov et al. | |
| 6,306,628 B1 * | 10/2001 | Rothschild et al. | ......... 435/91.3 |
| 2005/0032078 A1 * | 2/2005 | Rothschild et al. | ............. 435/6 |

FOREIGN PATENT DOCUMENTS

| EP | 0152483 A1 | 8/1985 |
| GB | 2183661 A | 6/1987 |
| JP | 4-200390 A | 7/1992 |
| JP | 7-110236 B2 | 11/1995 |
| WO | WO 90/05785 A1 | 5/1990 |
| WO | WO 91/05058 A1 | 4/1991 |
| WO | WO 98/21353 A1 | 5/1998 |

OTHER PUBLICATIONS

Shimizu et al., "Cell-free translation reconstituted with purified components", 2001, Nature Biotechnology, 19, 751-755.*
Lutz Jermutus et al., Current Opinion in Biotechnology, vol. 9, (1998), pp. 534-548.
Wolfgang Stiege et al., Journal of Biotechnology, vol. 41, (1995), pp. 81-90.
Elizabeth A. Burks et al., Proc. Natl. Acad. Sci. USA, vol. 94, (Jan. 1997), pp. 412-417.
Kirill A. Martemyanov et al., FEBS Letters, vol. 414, (1997), pp. 268-270.
David Mendel, Annu. Rev. Biophys. Biomol. Struct., vol. 24, (1995), pp. 435-462.
Mingyue He et al., Journal of Immunological Methods, vol. 231, (1999), pp. 105-117.
Christiane Schaffitzel et al., Journal of Immunological Methods, vol. 231, (1999), pp. 119-135.
Richard W. Roberts, Current Opinion in Chemical Biology, vol. 3, (1999), pp. 268-273.
Bruce M. Paterson et al., Proc. Natl. Acad. Sci. USA, vol. 74, No. 10, (Oct. 1977), pp. 4370-4374.
Eva J. Helmerhorst et al., FEBS Letters, vol. 449, (1999), pp. 105-110.
Jozef Hanes et al, Proc. Natl. Acad. Sci. USA, vol. 95, (Nov. 1998), pp. 14130-14135.
Jozef Hanes et al., Proc. Natl. Acad. Sci. USA, vol. 94, (May 1997), pp. 4937-4942.
Deborah A. Steege, RNA (2000), vol. 6, pp. 1079-1090.
S.V. Matveev et al., Biochem. Biophys. Acta, vol. 1293, (1996), pp. 207-212.
Yoshihisa Kitaoka et al., Journal of Biotechnology, vol. 48, (1996), pp. 1-8.
Joseph D. Mosca et al., Biochemistry, vol. 22, (1983), pp. 346-354.
John A. Hucul et al., The Journal of Biological Chemistry, vol. 260, No. 29, (Dec. 15, 1985), pp. 15585-15591.
Shui-Liang Yao et al., Journal of Fermentation and Bioengineering, vol. 84, No. 1, (1997), pp. 7-13.
Yasuaki Kawarasaki et al., Journal of Biotechnology, vol. 61, (1998), pp. 199-208.
Nicholas D. Hastie et al., Proc. Natl. Acad. Sci. USA, vol. 75, No. 3, (Mar. 1978), pp. 1217-1221.
Hsiang-Fu Kung et al., The Journal of Biological Chemistry, vol. 252, No. 19, (Oct. 10, 1977), pp. 6889-6894.
R.H. Green et al., Biochemical and Biophysical Research Communications, vol. 126, No. 2, (Jan. 31, 1985), pp. 792-798.
Michael Yu. Pavlov et al., Archives of Biochemistry and Biophysics, vol. 328, No. 1, (Apr. 1, 1996), pp. 9-16.
Michael Yu. Pavlov et al., J. Mol. Biol., vol. 273, (1997), pp. 389-401.
Kathy Boon et al., Eur. J. Biochem., vol. 210, (1992), pp. 177-183.
Kevin S. Wilson et al., Cell, vol. 92, (1998), pp. 131-139.
Yu-Wen Hwang et al., Archives of Biochemistry and Biophysics, vol. 348, No. 1, (Dec. 1, 1997), pp. 157-162.

(Continued)

*Primary Examiner*—Robert A. Wax
*Assistant Examiner*—Suzanne M. Noakes
(74) *Attorney, Agent, or Firm*—Birch, Stewart, Kolasch & Birch, LLP

(57) ABSTRACT

The present invention relates to a reaction system whereby a peptide produced in an in vitro peptide synthesis system can be efficiently isolated at a high purity from the reaction system. Thus the present invention is a process for producing a peptide or a peptide derivative by using a reaction system of transcribing a DNA into an RNA and then translating the RNA produced or a reaction system of translating an RNA in vitro wherein at least one protein component of the reaction system is labeled with a first substance which adheres to a second substance, and said second substance is used as an adsorbent for capturing said labeled protein components after translating.

17 Claims, 12 Drawing Sheets

OTHER PUBLICATIONS

Koichi Ito et al., Proc. Natl. Acad. Sci. USA, vol. 95, (Jul. 1998), pp. 8165-8169.
Armin Lechler et al., Protein Expression and Purification, vol. 8, (1996), pp. 347-357.
Takanori Kigawa et al., Proteins, Nucleic Acid and Enzymes/Partial Translation, vol. 44, (1999), pp. 598-605.
Nobutoshi Chikazumi et al., Bio Industry/Partial Translation, vol. 8, (1991), pp. 749-759.
Poul Nissen et al., SCIENCE, vol. 289, (Aug. 11, 2000), pp. 920-930.
Claudio O. Gualerzi et al., Biochemistry, vol. 29, No. 25, (Jun. 26, 1990), pp. 5881-5889.
Tillmann Pape et al., The EMBO Journal, vol. 17, No. 24, (1998), pp. 7490-7497.
Rajendra K. Agrawal et al., Nature Structural Biology, vol. 6, No. 7, (Jul. 1999), pp. 643-647.
Marina V. Rodnina et al., FEMS Microbiology Reviews, vol. 23, (1999), pp. 317-333.
David V. Freistroffer et al., The EMBO Journal, vol. 16, No. 13, (1997), pp. 4126-4133.
Michael Yu. Pavlov et al., The EMBO Journal, vol. 16, No. 13, (1997), pp. 4134-4141.
Christopher Francklyn et al., RNA, vol. 3, (1997), pp. 954-960.
Osamu Nureki et al., Proteins, Nucleic Acids and Enzymes/Partial Translation, vol. 39, No. 7, (1994), pp. 1215-1225.
Vaidyanathan Ramesh et al., Proc. Natl. Acad. Sci. USA, vol. 96, (Feb. 1999), pp. 875-880.
Tanya Zarucki-Schulz et al., Proc. Natl. Acad. Sci. USA, vol. 76, No. 12, (Dec. 1979), pp. 6115-6119.
Eitaro Yasumitsu et al., Proteins Experiment Note/Partial Translation, Chap. 5-2, (1999), pp. 139-161.
Joshua A. Bornhorst et al., Methods in Enzymology, vol. 326, (2000), pp. 245-254.
Patrick J. Farrell et al., PROTEINS: Structure, Function, and Genetics, vol. 41, (2000), pp. 144-153.
Mark A. Schembri et al., FEMS Microbiology Letters, vol. 188, (2000), pp. 147-151.
Maris V. Fonseca et al., Journal of Bacteriology, vol. 182, (2000), pp. 4304-4309.
Michael W. Van Dyke et al., Gene, vol. 111, (1992), pp. 99-104.
David C. Kaslow et al., Bio/Technology, vol. 12, (May 1994), pp. 494-499.
Ralf Janknecht et al., Gene, vol. 121, (1992), pp. 321-324.
Arja Kuusinen et al., Eur. J. Biochem., vol. 233, (1995), pp. 720-726.
Ali Alejo et al., The Journal of Biological Chemistry, vol. 272, No. 14, (Apr. 4, 1997), pp. 9417-9423.
Rajendar Deora et al., Journal of Bacteriology, vol. 179, No. 20, (Oct. 1997), pp. 6355-6359.
Pamela J. Woodring et al., The Journal of Biological Chemistry, vol. 272, No. 48, (Nov. 28, 1997), pp. 30447-30454.
Bjorn Nilsson et al., Methods in Enzymology, vol. 185, (1990), pp. 144-161.
Robert S. Molday et al., Methods in Enzymology, vol. 294, (1999), pp. 246-261.
Arne Skerra et al., Methods in Enzymology, vol. 326, (2000), pp. 271-304.
A.P. Alimov et al., BioTechniques, vol. 28, No. 2, (2000), pp. 338-344.
Ronald T. Raines et al., Methods in Enzymology, vol. 326, (2000), pp. 362-376.
Peter Vaillancourt et al., Methods in Enzymology, vol. 326, (2000), pp. 340-362.
Torbjorn Graslund et al., Protein Expression and Purification, vol. 9, (1997), pp. 125-132.
Tsutomu Suetake et al., Protein Experiment Note/Partial Translation, Chap. 5-1, (1999), pp. 162-166.
Donald B. Smith, Methods in Enzymology, vol. 326, (2000), pp. 254-270.
R.K. Scopes et al., Analytical Biochemistry, vol. 136, (1984), pp. 530-534.
Juan de Dios Alche et al., Protein Expression and Purification, vol. 12, (1998), pp. 138-143.
Deepali Sachdev et al., Methods in Enzymology, vol. 326, (2000), pp. 312-321.
Chung-Mo Park et al., Biochemistry, vol. 39, (2000), pp. 6349-6356.
J.C. Smith et al., Gene, vol. 32, (1984), pp. 321-327.
Sonoko Kobayashi et al., J. Biochem., vol. 117, (1995), pp. 758-765.
Pierre C. Jelenc et al., Proc. Natl. Acad. Sci. USA, vol. 76, No. 7, (Jul. 1979), pp. 3174-3178.
E. Gerhart H. Wagner et al., Eur. J. Biochem., vol. 122, (1982), pp. 193-197.
Joanne Crow et al., Methods in Molecular Biology, vol. 31, Chapter 35, (1994), pp. 371-387.
E. Hochuli et al., Journal of Chromatography, vol. 411, (1987), pp. 177-184.
Donald B. Smith et al., Gene, vol. 67, (1988), pp. 31-40.
Alexander S. Spirin et al., SCIENCE, vol. 242, (1998), pp. 1162-1164.
Don-Myung Kim et al., Biotechnol. Prog., vol. 12, (1996), pp. 645-649.
M. Clelia Ganoza et al., Proc. Natl. Acad. Sci. USA, vol. 82, (Mar. 1985), pp. 1648-1652.
Jean-Michel Guillon et al., Journal of Bacteriology, vol. 174, No. 13, (Jul. 1992), pp. 4294-4301.
Rob Benne et al., Biochem. Biophys. Acta, vol. 269, (1972), pp. 304-310.
Daniel E. Atkinson, Biochemistry, vol. 7, (1968), pp. 4030-4034.
Christopher J. Noren et al., SCIENCE, vol. 244, (1989), pp. 182-188.
Dong-Myung Kim et al., Eur. J. Biochem., vol. 239, (1996), pp. 881-886.
Bernard R. Glick et al., Proc. Natl. Acad. Sci. USA, vol. 72, No. 11, (Nov. 1975), pp. 4257-4260.
Hans Kossel, Biochem. Biophys. Acta, vol. 204, (1970), pp. 191-202.
Jie Lu et al., The International Journal of Biochemistry & Cell Biology, vol. 31, (1999), pp. 215-229.
Hsiang-Fu Kung et al., Proc. Natl. Acad. Sci. USA, vol. 74, No. 8, (Aug. 1977), pp. 3217-3221.
Peter O. Olins et al., The Journal of Biological Chemistry, vol. 264, No. 29, (Oct. 15, 1989), pp. 16973-16976.
Jeffrey R. Sampson et al., Proc. Natl. Acad. Sci. USA, vol. 85, (Feb. 1988), pp. 1033-1037.
Martin Poe et al., Biochemistry, vol. 11, No. 6, (1972), pp. 1023-1030.
Robert F. Schleif, J. Mol. Biol., vol. 61, (1971), pp. 275-279.
Glenn F. Short III et al., Biochemistry, vol. 38, (1999), pp. 8808-8819.
Y. Endo, *Bio Industry*, partial translation, vol. 17, pp. 20-27 (2000).
K. Watanabe, *Bioscience and Industry*, partial translation, vol. 47, No. 10, pp. 16-24 (1989).
Schmidt et al., *Protein Engineering*, vol. 6, No. 1, pp. 109-122 (1993).
Schmidt et al., *J. Mol. Biol.*, vol. 255, pp. 753-766 (1996).
G. Spedding, *Ribosomes and Protein Synthesis, A Practical Approach*, (IRL Press at Oxford University Press), pp. 1-29 (1990).
Lynch, *Methods in Enzymology*, vol. 152, pp. 248-253 (1987).
Krawetz et al., *Can J. Biochem Cell Biol*, vol. 61, pp. 274-286 (1983).
Kozak, *Nucleic Acids Research*, vol. 15, pp. 8125-8148 (1987).
Lizardi et al., *Biotechnology*, vol. 6, pp. 1197-1202 (1988).
Krieg et al., *Nucleic Acids Research*, vol. 12, No. 18, pp. 7057-7070 (1984).
Rogers et al., *Proc. Natl. Acad. Sci. USA*, vol. 82, pp. 5218-5222 (1985).
Bottomley et al., *Eur. J. Biochem.*, vol. 93, pp. 31-39 (1979).
Ackers et al., *Ann. Rev. Biochem.*, vol. 54, pp. 597-629 (1985).
Schimmel et al., *Ann. Rev. Biochem.*, vol. 48, pp. 601-648 (1979).
Murgola, *Ann. Rev. Genet.*, vol. 19, pp. 57-80 (1985).
Heckler et al., *The Journal of Biological Chemistry*, vol. 258, No. 7, pp. 4492-4495 (1983).

Roesser et al., *Biochemistry*, vol. 25, pp. 6361-6365 (1986).
Baldini et al., *Biochemistry*, vol. 27, pp. 7951-7959 (1988).
Heikkila et al., *Acta Chemica Scandinavica B*, vol. 37, pp. 857-864 (1983).
Kwok et al., *Can J. Biochem*, vol. 58, pp. 213-218 (1980).
Bruce et al., *Proc. Natl. Acad. Sci USA*, vol. 79, pp. 7127-7131 (Dec. 1982).
Heckler et al., *Tetrahedron*, vol. 40, No. 1, pp. 87-94 (1984).
Ryabova et al., *Anal. Biochem*, vol. 226, pp. 184-186 (1995).
Jacques et al., *Molecular Microbiology*, vol. 4, No. 7, pp. 1063-1067 (1990).
Sprengart et al., *Molecular Microbiology*, vol. 24, No. 1, pp. 19-28 (1997).
Yamamoto et al., *J. Chem. Eng. Japan*, vol. 29, No. 6, pp. 1047-1050 (1996).
Das et al., *Eur. J. Biochem.*, vol. 235, pp. 613-621 (1996).
Chattopadhyay et al., *Proc. Natl. Acad. Sci. USA*, vol. 93, pp. 8284-8287 (1996).
Kramer et al., *Methods Enzymol*, vol. 290, pp. 18-26 (1998).
Phizicky et al., *Microbiological Reviews*, vol. 59, No. 1, pp. 94-123 (1995).
Mattheakis et al., *Methods in Enzymology*, vol. 267, pp. 195-207 (1996).
Roberts et al., *Proc. Natl. Acad Sci, USA*, vol. 94, pp. 12297-12302 (1997).
Romit Majumdar et al., *Nucleic Acids Research*, vol. 30, No. 5, (2002), pp. 1154-1162.
Amitabha Bandyopadhyay et al., *The Journal of Biological Chemistry*, vol. 277, No. 3, (Jan. 18, 2002), pp. 2360-2367.
Sharon Mcgonigle et al., *Biochemistry*, vol. 41, (2002), pp. 579-587.
Ivan Ventoso et al., PNAS, vol. 98, No. 23, (Nov. 6, 2001), pp. 12966-12971.
Xavier Saelens et al., *The Journal of Biological Chemistry*, vol. 276, No. 45, (Nov. 9, 2001), pp. 41620-41628.
Wei Li et al., FEBS Letters, vol. 507, (2001), pp. 1-5.
Linda Mckendrick et al., *Eur. J. Biochem*, vol. 268, (2001), pp. 5375-5385.
Dezemona Petrelli et al., *The EMBO Journal*, vol. 20, No. 16, (2001), pp. 4560-4569.
Iraj K. Ali et al., *The EMBO Journal*, vol. 20, No. 15, (2001), pp. 4233-4242.
Wei Li et al., *The Journal of Biological Chemistry*, vol. 276, No. 31, (Aug. 3, 2001), pp. 29111-29115.
Francisco Campos et al., *The Journal of Biological Chemistry*, vol. 276, No. 30, (Jul. 27, 2001), pp. 28388-28394.
José-Manuel Mingot et al., *The EMBO Journal*, vol. 20, No. 14, (2001), pp. 3685-3694.
Thanuja Krishnamoorthy et al., *Molecular and Cellular Biology*, vol. 21, No. 15, (Aug. 2001), pp. 5018-5030.
Martin Bushell et al., *The Journal of Biological Chemistry*, vol. 276, No. 26, (Jun. 29, 2001), pp. 23922-23928.
Tzann-Wei Wang et al., *The Journal of Biological Chemistry*, vol. 276, No. 20, (May 18, 2001), pp. 17541-17549.
Nadia L. Korneeva et al., *The Journal of Biological Chemistry*, vol. 276, No. 4, (Jan. 26, 2001), pp. 2872-2879.
Linda Mckendrick et al., *Molecular and Cellular Biology*, vol. 21, No. 11, (Jun. 2001), pp. 3632-3641.
Katsura Asano et al., *The EMBO Journal*, vol. 20, No. 9, (2001), pp. 2326-2337.
Diana Dominguez et al., *Biochem. J.*, vol. 355, (2001), pp. 223-230.
Supratik Das et al, *The Journal of Biological Chemistry*, vol. 276, No. 9, (Mar. 2, 2001), pp. 6720-6726.
Uttiya Basu et al, *Molecular and Cellular Biology*, vol. 75, No. 5, (Mar. 2001), pp. 1453-1462.
Joseph Nika et al, *The Journal of Biological Chemistry*, vol. 276, No. 2, (Jan. 12, 2001), pp. 1051-1056.
Joseph Marcotrigiano et al., *Molecular Cell*, vol. 7, (Jan. 2001), pp. 193-203.
Fiona E.M. Paulin et al., *Current Biology*, vol. 11, No. 1, (2001), pp. 55-59.
Avital Yahalom et al., *The Journal of Biological Chemistry*, vol. 276, No. 1, (Jan. 5, 2001), pp. 334-340.
Seong-Whan Park et al, *Mol. Cells*, vol. 10, No. 6, (2000), pp. 626-632.
Da-Qing Yang et al., *Nature Cell Biology*, vol. 2, (Dec. 2000), pp. 893-898.
Nadia L. Korneeva et al, *The Journal of Biological Chemistry*, vol. 275, No. 52, (Dec. 29, 2000), pp. 41369-41376.
David C. Schwartz et al., *Molecular and Cellular Biology*, vol. 20, No. 21, (Nov. 2000), pp. 7933-7942.
Tobias von der Haar et al., *The Journal of Biological Chemistry*, vol. 275, No. 39, (Sep. 29, 2000), pp. 30551-30555.
Katsura Asano et al., *Genes & Development*, vol. 14, (2000), pp. 2534-2546.
Tracy G. Anthony et al., *Biochimica et Biophysica Acta*, vol. 1492, (2000), pp. 56-62.
Cristine Vilela et al., *The EMBO Journal*, vol. 19, No. 16, (2000), pp. 4372-4382.
Gerd Lipowsky et al., *The EMBO Journal*, vol. 19, No. 16, (2000), pp. 4362-4371.
Simon Léonard et al., *Journal of Virology*, vol. 74, No. 17, (Sep. 2000), pp. 7730-7737.
Evgeny V. Pilipenko et al., *Genes & Development*, vol. 14, (2000), pp. 2028-2045.
Terence P. Herbert et al., *Current Biology*, vol. 10, No. 13 (2000), pp. 793-796.
Chia-Lung Hou et al., *Blood*, vol. 96, No. 2, (Jul. 15, 2000), pp. 747-753.
Victoria G. Kolupaeva et al, *Journal of Virology*, vol. 74, No. 14, (Jul. 2000), pp. 6242-6250.
Zan Xu et al., *Molecular and Cellular Biology*, vol. 20, No. 14, (Jul. 2000), pp. 5285-5299.
Xiping Bi et al., *The Journal of Biological Chemistry*, vol. 275, No. 23, (Jun. 9, 2000), pp. 17740-17746.
Edith Gomez et al., *Molecular and Cellular Biology*, vol. 20, No. 11, (Jun. 2000), pp. 3965-3976.
Supratik Das et al, *Molecular and Cellular Biology*, vol. 20, No. 11, (Jun. 2000), pp. 3942-3950.
Xiping Bi et al., *Biochemistry*, vol. 39, (2000), pp. 5758-5765.
Glória M. Thompson et al., *Biochem. J.*, vol. 347, (2000), pp. 703-709.
Bryan Mcintosh et al., *Biochimie*, vol. 82, (2000), pp. 167-174.
Vijay Kumar et al., *The Journal of Biological Chemistry*, vol. 275, No. 15, (Apr. 14, 2000), pp. 10779-10787.
Tapan Maiti et al., *Gene*, vol. 244, (2000), pp. 109-118.
John L. Battiste et al., *Molecular Cell*, vol. 5, (Jan. 2000), pp. 109-119.
Shigenobu Morino et al., *Molecular and Cellular Biology*, vol. 20, No. 2, (Jan. 2000), pp. 468-477.
Dietrich Ober et al., PNAS, vol. 96, No. 26, (Dec. 21, 1999), pp. 14777-14782.
Nancy J. Richter et al., *The Journal of Biological Chemistry*, vol. 274, No. 50, (Dec. 10, 1999), pp. 35415-35424.
Dietrich Ober et al., *The Journal of Biological Chemistry*, vol. 274, No. 45, (Nov. 5, 1999), pp. 32040-32047.
Qiyu Li et al., *Molecular and Cellular Biology*, vol. 19, No. 11, (Nov. 1999), pp. 7336-7346.
Dorothea K. Thompson et al., *Molecular Microbiology*, vol. 33, No. 5, (1999), pp. 1081-1092.
Diana Dominguez et al., *The Journal of Biological Chemistry*, vol. 274, No. 38, (Sep. 17, 1999), pp. 26720-26726.
Sheri Uma et al., *Molecular and Cellular Biology*, vol. 19, No. 9, (Sep. 1999), pp. 5861-5871.
Stuart A. Wilson et al., *Biochem. J.*, vol. 342, (1999), pp. 97-103.
Juan Manuel Palacios Moreno et al., FEBS Letters, vol. 455, (1999), pp. 130-134.
Marina Ptushkina et al., *The EMBO Journal*, vol.18, No. 14, (1999), pp. 4068-4075.
Panda E. C. Hershey et al., *The Journal of Biological Chemistry*, vol. 274, No. 30, (Jul. 23, 1999), pp. 21297-21304.
Carrie L. Neff et al., *Molecular and Cellular Biology*, vol. 19, No. 8, (Aug. 1999), pp. 5557-5564.
Nathalie Methot et al., *Molecular and Cellular Biology*, vol. 14, No. 4, (Apr. 1994), pp. 2307-2316.

Stéphanie Kervestin et al., EMBO reports, vol. 2, No. 8, (2001), pp. 680-684.
Alim Seit-Nebi et al., *Nucleic Acids Research*, vol. 29, No. 19, (2001), pp. 3982-3987.
Kevin S. Wilson et al., *Nature Structural Biology*, vol. 7, No. 10, (Oct. 2000), pp. 866-870.
Kevin Czaplinski et al., *RNA*, vol. 6, (2000), pp. 730-743.
Maria Dontsova et al., FEBS Letters, vol. 472, (2000), pp. 213-216.
Ludmila Yu. Frolova et al., *RNA*, vol. 6, (2000), pp. 381-390.
Ludmila Yu. Frolova et al., *RNA*, vol. 5, (1999), pp. 1014-1020.
Kanae Ebihara et al., *RNA*, vol. 5, (1999), pp. 739-750.
Lily Eurwilaichitr et al., *Molecular Microbiology*, vol. 32, No. 3, (1999), pp. 485-496.
Tatyana I. Merkulova et al., FEBS Letters, vol. 443, (1999), pp. 41-47.
Lyudmila Y. Frolova et al., *Eur. J. Biochem.*, vol. 256, (1998), pp. 36-44.
Koichi Ito et al., *RNA*, vol. 4, (1998), pp. 958-972.
Koichi Ito et al., *Proc. Natl. Acad. Sci.*, vol. 95, (Jul. 1998), pp. 8165-8169.
Kevin Czaplinski et al., Genes & Development, vol. 12, (1998), pp. 1665-1677.
K. Ito et al., *Biochimie*, vol. 79, (1997), pp. 287-292.
Xavier Goff et al., *Molecular and Cellular Biology*, vol. 17, No. 6, (Jun. 1997), pp. 3164-3172.
Sergey V. Paushkin et al., *Molecular and Cellular Biology*, vol. 17, No. 5, (May 1997), pp. 2798-2805.
M. Uno et al., *Biochimie*, vol. 78, (1996), pp. 935-943.
Yoichi Kawazu et al., *Journal of Bacteriology*, vol. 177, No. 19, (Oct. 1995), pp. 5547-5553.
Luba Timchenko et al., *Proc. Natl. Acad. Sci.*, vol. 91, (Mar. 1994), pp. 2777-2780.
Craig M. Johnson et al., *Journal of General Virology*, vol. 82, (2001), pp. 2935-2943.
Ruth Furukawa et al., *Biochimica at Biophysica Acta*, vol. 1527, (2001), pp. 130-140.
Lian N. Olsthoorn-Tieleman et al., *European Journal of Biochemistry*, vol. 268, No. 13, (Jul. 2001), pp. 3807.
Kouji Nakamura et al., *The Journal of Biological Chemistry*, vol. 276, No. 25, (Jun. 22, 2001), pp. 22844-22849.
Takashi Ohtsuki et al., *The Journal of Biological Chemistry*, vol. 276, No. 24, (Jun. 15, 2001), pp. 21571-21577.
Eulàlia de Nadal et al., *The Journal of Biological Chemistry*, vol. 276, No. 18, (May 4, 2001), pp. 14829-14834.
Choukri Ben Mamoun et al., *Molecular Microbiology*, vol. 39, (2001), pp. 973-981.
Tricia A. Diggle et al., *Biochem. J.*, vol. 353, (2001), pp. 621-626.
Guennadi Kozlov et al., *Journal of Biomolecular NMR*, vol. 17, (2000), pp. 187-194.
Ryan Bingham et al., *The Journal of Biological Chemistry*, vol. 275, No. 30, (Jul. 28, 2000), pp. 23219-23226.
Anne Carr-Schmid et al., *Molecular and Cellular Biology*, vol. 19, No. 8, (Aug. 1999), pp. 5257-5266.
Andrea Cimarelli et al., *Journal of Virology*, vol. 73, No. 7, (Jul. 1999), pp. 5388-5401.
Oleh Kovalchuke et al., *Eur. J. Biochem.*, vol. 258, (1998), pp. 986-993.
Shin-ichiro Kidou et al., FEBS Letters, vol. 434, (1998), pp. 382-386.
Martina Nesper et al., *Eur. J. Biochem.*, vol. 255, (1998), pp. 81-86.
Masato Umikawa et al., *Oncogene*, vol. 16, (1998), pp. 2011-2016.
T. Georgiou et al., *Proc. Natl. Acad. Sci.*, vol. 95, (Mar. 1998), pp. 2891-2895.
Yasushi Kawaguchi et al., *Journal of Virology*, vol. 71, No. 2, (Feb. 1997), pp. 1019-1024.
M. Kromayer et al., *J. Mol. Biol.*, vol. 262, (1996), pp. 413-420.
Anneke Talens et al., *Biochemical and Biophysical Research Communications*, vol. 225, No. 1279, (1996), pp. 961-967.
Constantinos Stathopoulos et al., PNAS, vol. 98, No. 25, (Dec. 4, 2001), pp. 14292-14297.
Hongfang Qiu et al., *The EMBO Journal*, vol. 20, No. 6, (2001), pp. 1425-1438.
Shipra Bunjun et al., PNAS, vol. 97, No. 24, (Nov. 21, 2000), pp. 12997-13002.
David R. Liu et al., *Proc. Natl. Acad. Sci.*, vol. 94, (Sep. 1997), pp. 10092-10097.
G. Paravicini et al., *Biochemical and Biophysical Research Communications*, vol. 227, (1996), pp. 82-87.
Takuya Ueda et al., *Nucleic Acids Research*, vol. 19, No. 3, (1991), pp. 547-552.
Hideki Tohda et al., *Journal of Biotechnology*, vol. 34, (1994), pp. 61-69.
Yoshihiro Shimizu et al., *Biochemistry/Seikagaku* (The Japanese Biochemical Society), vol. 71, No. 8, (Aug. 25, 1999), pp. 1085. Translation of Document 244.
Yoshihiro Shimizu, Translation of Presentation in 1999, not published (Document No. 245).
Yoshihiro Shimizu et al., Translation of Presentation, not published, The 2$^{nd}$ RNA Meeting, (Jul. 31-Aug. 2, 2000), Shinagawa Prince Hotel Annex, Tokyo (Document No. 246).
Yoshihiro Shimizu et al., Partial translation of Presentation, 2000, not published (Document No. 247).
Yoshihiro Shimizu et al., *Nature Biotechnology*, vol. 19, (Aug. 2001), pp. 751-755.
Putney, S.D. et al., "E. coli alas gene coding for alanyl-tRNA synthetase." GenBank Accession No. J01581, (Nov. 9, 1993).
Gangloff, J., "*Escherichia coli* argS gene for arginyl-tRNA-synthetase." GenBank Accession No. X15320, (Feb. 10, 1999).
Anselme, J. et al., "*E. coli* asparaginyl-tRNA synthetase (asnS) gene, complete cds." GenBank Accession No. M33145, (Apr. 26, 1993).
Eriani, G., "*E. coli* asps gene for aspartyl-tRNA synthetase." GenBank Accession No. X53863, (Jan. 28, 1991).
Eriani, G., "*E. coli* cysS gene for cysteinyl-tRNA synthetase." GenBank Accession No. X56234, (Feb. 8, 1991).
Hoben, P. et al., "*E. coli* glutaminyl-tRNA synthetase (glnS) gene, complete cds." Accession No. J01617, (Feb. 14, 1996).
Breton, R., "*Escherichia coli* K12 valU, gltX and alaW region." GenBank Accession No. X63976, (May 5, 1995).
Webster T.A. et al., "*E. coli* glyS gene coding for glycyl-tRNA synthetase alpha-and beta-subunits." GenBank Accession No. J01622, (Apr. 26, 1993).
Freedman, R., "*Escherichia coli* histidine-tRNA synthetase (hisS), complete cds." GenBank Accession No. M11843, (Feb. 11, 2002).
Mori, H., "*Escherichia coli* genomic DNA." GenBank Accession No. D10483, (May 29, 2002).
Haertlein, M., "*E. coli* leuS gene for leucyl-trna synthetase." GenBank Accession No. X06331, (Sep. 12, 1993).
Dessen, P., "*Escherichia coli* lysU gene for lysyl-tRNA synthetase (EC 6.1.1.6)." GenBank Accession No. X16542, (Sep. 9, 1993).
Dardel, F. et al., "*E. coli* metG gene coding for methionyl-tRNA synthetase, complete cds." GenBank Accession No. K02671, (Jan. 3, 2001).
Mechulam, Y. et al., "*E. coli* thrS, infC, rplT, pheS, pheT and himA genes encoding threonyl-tRNA synthetase, initiation factor IF3, ribosomal protein L20, phenylalanyl-tRNA synthetase and the alpha-subunit of the host integration factor." GenBank Accession No. V00291, (Nov. 30, 1997).
Eriani, G. et al., "*Escherichia coli* prolyl-tRNA synthetase (proS) gene, complete cds." GenBank Accession No. M97858, (Apr. 26, 1993).
Hartlein, M. et al., "*E. coli* serS gene for seryl-tRNA synthetase." GenBank Accession No. X05017, (Sep. 12, 1993).
Mayaux, J.F. et al., "*E. coli* thrS, infC, rplT, pheS, pheT and himA genes encoding threonyl-tRNA synthetase, initiation factor IF3, ribosomal protein L20, phenylalanyl-tRNA synthetase and the alpha-subunit of the host integration factor." GenBank Accession No. V00291, (Nov. 30, 1997).
Sever, S. et al., "*Escherichia coli* tryptophanyl-tRNA synthetase (trpS) gene, complete cds." GenBank Accession No. U38647, (Mar. 15, 1996).
Barker, D.G. et al., "*E. coli* tyrS gene coding for tyrosyl-tRNA synthetase." GenBank Accession No. J01719, (Apr. 26, 1993).

Heck, J.D. et al., "*E. coli* valS gene encoding valyl-tRNA synthetase gene, complete cds." GenBank Accession No. J03497, (Apr. 26, 1993).

Mechulam, Y., "*E. coli* fmt gene for L-methionyl-tRNAMetf N-formyltransferase." GenBank Accession No. X63666, (Feb. 17, 1997).

Cummings, H.S., "*E. coli* infA gene for initiation factor Ifl." GenBank Accession No. Y00373, (Sep. 12, 1993).

Blattner, F.R. et al., "*Escherichia coli* K12 MG1655 section 287 of 400 of the complete genome." GenBank Accession No. AE000397, (Dec.1, 2000).

Sacerdot, C. et al., "*E. coli* thrS, infC, rplT, pheS, pheT and himA genes encoding threonyl-tRNA synthetase, initiation factor IF3, ribosomal protein L20, phenylalanyl-tRNA synthetase and the alpha-subunit of the host integration factor." GenBank Accession No. V00291, (Nov. 30, 1997).

Zengel, J.M., "*E. coli* fus gene encoding elongation factor G." GenBank Accession No. X00415, (Aug. 9, 1994).

An, G. et al., "*E. coli* tufB gene for translation elongation factor EF-Tu." GenBank Accession No. X57091, (May 5, 1993).

An, G. et al., "*E. coli* genes tsf and rpsB, encoding factor Ts and ribosomal protein S2." GenBank Accession No. V00343, (Jan. 18, 2002).

Nakayashiki, T., "*E. coli* prfA gene encoding peptide chain release factor 1 (RFl)." GenBank Accession No. D28567, (Feb. 7, 1999).

Grentzmann, G. et al., "*E. coli* prfC gene for peptide termination factor." GenBank Accession No. Z26313, (Sep. 15, 1994).

Ichikawa, S. et al., "*E. coli* ribosome releasing factor gene, complete cds." GenBank Accession No. J05113, (Apr. 26, 1993).

Grachev, M.A. et al., "Bacteriophage T7 RNA polymerase gene, complete cds." GenBank Accession No. M38308, (Apr. 28, 1993).

Hama, H., "*E. coli* NDK gene for nucleoside diphosphate kinase." GenBank Accession No. X57555, (Jan. 20, 1997).

Gonin, P. et al., Biochemistry, vol. 38, pp. 7265-7272 (1999).

Ogura, Y. et al., Eur. J. Biochem., vol. 266, pp. 709-714 (1999).

Barthel, T. et al., The Journal of Biochemical Chemistry, vol. 274(51), pp. 36670-36678 (1999).

Klinker, J.F. et al.,Eur. J. Biochem., vol. 261, pp. 72-80 (1999).

Prinz, H. et al., The Journal of Biological Chemistry, vol. 274, No. 50, pp. 35337-35342 (1999).

Schaertl, S. et al., The Journal of Biological Chemistry, vol. 274, No. 29, pp. 20159-20164 (1999).

Milon, L. et al., The Journal of Biological Chemistry, vol. 275, No. 19, pp. 14264-14272 (2000).

Ogura, Y. et al., The Journal of Biological Chemistry, vol. 276, No. 24, pp. 21228-21234 (2001).

Schaertl, S. et al., The Journal of Biological Chemistry, vol. 273, No. 10, pp. 5662-5669 (1998).

Munier, A. et al., FEBS Letters, vol. 434, pp. 289-294 (1998).

Engel, M. et al., The Journal of Biological Chemistry, vol. 273, No. 32, pp. 20058-20065 (1998).

Yano, M. et al., FEBS Letters, vol. 419, pp. 244-248 (1997).

Ishijima, Y. et al., FEBS Letters, vol. 445, pp. 155-159 (1999).

Cho, S-J. et al., Biochemical & Biophysical Research Communications, vol. 289, pp. 738-743 (2001).

Stephenson, K. et al., PNAS, vol. 98, No. 26, pp. 15251-15256 (2001).

Ishibashi, M. et al., FEBS Letters, vol. 493, pp. 134-138 (2001).

Ghadessy, F. et al., PNAS, vol. 98, No. 8, pp. 45552-4557 (2001).

Zhu, J. et al., PNAS, vol. 96, No. 26, pp. 14911-14918 (1999).

Tzeng, C-M. et al., The Journal of Biological Chemistry, vol. 275, No. 6, pp. 3977-3983 (2000).

Loisel, T. P. et al., Nature, vol. 401, pp. 613-616 (1999).

Song, J. S. et al., Biochemistry, vol. 39, pp. 10090-10097 (2000).

Otsuki, Y. et al., PNAS, vol 98, No. 8, pp. 4385-4390 (2001).

Schneider, B. et al., Molecular Pharmacology, vol. 57, pp. 948-953 (2000).

Chakrabarty, A. M. et al., Molecular Microbiology, vol. 28, No. 5, pp. 875-882 (1998).

Freije, J.M.P. et al., The Journal of Biological Chemistry, vol. 272, No. 9, pp. 5525-5532 (1997).

Webb, P. A. et al., Journal of Molecular Biology, vol. 251, pp. 574-587 (1995).

Okabe-Kado, J. et al., Biochimica et Biophysica Acta, vol. 1267, pp. 101-106 (1995).

Chang, C. L. et al., Oncogene, vol. 12, pp. 659-667 (1996).

Ellinger, T., BioTechniques, vol. 24, pp. 718-720 (1998).

Kuderova, A. et al., Protein Expression and Purification, vol. 16, pp. 405-409 (1999).

Jebai, F. et al., Protein Expression and Purification, vol. 11, pp. 185-194 (1997).

Poterszman, A. et al., Protein Expression and Purification, vol. 9, pp. 153-158 (1997).

He, B. et al., Protein Expression and Purification, vol. 9, pp. 142-151 (1997).

Ghosh, S. et al., GENE, vol. 176, pp. 249-255 (1996).

Arnaud, N. et al., GENE, vol. 199, pp. 149-156 (1997).

Aniskovitch, L. P. et al., Microbiology, vol. 142, pp. 901-906 (1996).

Allen, S. V. et al., Analytical Biochemistry, vol. 269, pp. 32-37 (1999).

Garg, R. P. et al., Biochemistry, vol. 35, pp. 6297-6301 (1996).

Baier, G. et al., BioTechniques, vol. 17, No. 1, pp. 94-99 (1994).

Chiang, C-M. et al, The EMBO Journal, vol. 12, No. 7, pp. 2749-2762 (1993).

Tan, S. et al., Proc. Nat. Acad. Sci. USA, vol 91, pp. 9808-9812 (1994).

Yuryev, A. et al., Proc. Natl.Acad. Sc. USA, vol. 93, pp. 6975-6980 (1996).

Sakurai, H. et al., Proc. Natl. Acad. Sci. USA, vol. 93, pp. 9488-9482 (1996).

Reisenauer, A. et al., Journal of Bacteriology, vol. 178, No. 7, pp. 1919-1927 (1996).

McMahan, S. A. et al., Analytical Biochemistry, vol. 236, pp. 101-106 (1996).

Yankulov, K. Y. et al., Molecular and Cellular Biology, vol. 16, No. 7, pp. 3291-3299 (1996).

Lombardi, D. et al., Experimental Cell Research, vol. 217, pp. 267-271 (1995).

Mao, X. et al., Molecular and Cellular Biology, vol. 13, No. 12, pp. 7496-7506 (1993).

Tanaka, R. et al., Biosci. Biotechnol. Biochem., vol. 62, No. 9, pp. 1809-1811 (1998).

Fenno, J. C. et al., Journal of Bacteriology, vol. 178, No. 9, pp. 2489-2497 (1996).

Kalinich, J. F. et al., Protein Expression and Purification, vol. 5, pp. 324-330 (1994).

Huber, L. A. et al., Proc. Natl. Acad. Sci. USA, vol. 91, pp. 7874-7878 (1994).

Woychik, N. A. et al., Proc. Natl.Acad. Sci. USA, vol. 89, pp. 3999-4003 (1992).

Reddi, P. P. et al., GENE, vol 147, pp. 189-195 (1994).

Feldmann, H. et al., Virus Research, vol. 30, pp. 351-367 (1993).

Kigawa, T. et al., FEBS Letters, vol. 442, pp. 15-19 (1999).

Swartz, James, Nature Biology, vol. 19,, pp. 732-733 (2001).

Shimizu, Yoshihiro et al., The $2^{nd}$ RNA Meeting, (Jul. 31-Aug. 2, 2000), Shinagawa Prince Hotel Annex, Tokyo (Translation of Document No. 246).

Hongfang Qui et al., *The EMBO Journal*, vol. 20, No. 6, (2001), pp. 1425-1438.

John Augustine et al., *Biochemistry*, vol. 36, (1997), pp. 3473-3482.

Christopher Francklyn et al., *Journal Molecular Biology*, vol. 280, (1998), pp. 847-858.

Wen Yan et al., *Biochemistry*, vol 35, (1996), pp. 6559-6568.

Michael L. Bovee et al., *Biochemistry*, vol. 38, (1999), pp. 13725-13735.

Susan A. Hawko et al., *Biochemistry*, vol. 40, (2001), pp. 1930-1936.

Nemo M. Peeters et al., *Journal of Molecular Evolution*, vol. 50, (2000), pp. 413-423.

Melanie Beaulande et al., *Nucleic Acids Research*, vol. 26, No. 2, (1998), pp. 521-524.

Anne K. Kowal et al., *PNAS*, vol. 98, No. 5, (Feb. 27, 2001), pp. 2268-2273.

Constantinos Stathopoulos et al., *PNAS*, vol. 98, No. 25, (Dec. 4, 2001), pp. 14292-14297.

Shipra Bunjun et al., *PNAS*, vol. 97, No. 24, (Nov. 21, 2000), pp. 12997-13002.
Daisuke Kiga et al., *European Journal of Biochemistry*, vol. 268, (2001), pp. 6207-6213.
Hans-Ulrich Thomann et al., *Biotechnology*, vol. 14, (Jan. 1996), pp. 50-55.
Ho-Jin Park et al., *Molecular and Cellular Biology*, vol. 18, No. 8, (Aug. 1998), pp. 4418-4425.
Alexey D. Wolfson et al., *RNA*, vol. 4, (1998), pp. 1019-1023.
Martha A. Lovato et al., *The EMBO Journal*, vol. 20, No. 17, (2001), pp. 4846-4853.
Katsunori Hironaka et al., *The Journal of Biological Chemistry*, vol. 275, No. 21, (May 26, 2000), pp. 16167-16173.
Gregg B. Wells et al., *The Journal of Biological Chemistry*, vol. 276, No. 5, (Feb. 2, 2001), pp. 3031-3036.
Jian-Feng Chen et al., *Biochemistry*, vol. 39, (2000), pp. 6726-6731.
James M. Bullard et al., *Journal of Molecular Biology*, vol. 288, (1999), pp. 567-577.
Rupert Abele et al., *The Journal of Biological Chemistry*, vol. 273, No. 39, (Sep. 25, 1998), pp. 25132-25138.
Rene Jorgensen et al., *The Journal of Biological Chemistry*, vol. 275, No. 22, (Jun. 2, 2000), pp. 16820-16826.
Kyriaki Galani et al., *The EMBO Journal*, vol. 20, No. 23, (2001), pp. 6889-6898.
Guo-Qiang Chen et al., *Nature*, vol. 402, (Dec. 16, 1999), pp. 817-821.
Brian Burke et al., *Biochemistry*, vol. 39, (2000), pp. 15540-15547.
Catherine Stehlin et al., *Biochemistry*, vol. 36, (1997), pp. 2932-2938.
James M. Bullard et al., *Biochemica et Biophysica Acta*, vol. 1490, (2000), pp. 245-258.
Michael Ibba et al., *Science*, vol. 278, (Nov. 7, 1997), pp. 1119-1122.
Dieter Soll et al., *PNAS*, vol. 97, No. 26, (Dec. 19, 2000), pp. 14224-14228.
Keith D. Tardif et al., *Biochemistry*, vol. 40, (2001), pp. 8118-8125.
Brian Burke et al., *The Journal of Biological Chemistry*, vol. 276, No. 23, (Jun. 8, 2001), pp. 20286-20291.
Qiang Shan et al., *The Journal of Biological Chemistry*, vol. 276, No. 16, (Apr. 20, 2001), pp. 12556-12564.
Anne-Marie Duchene et al., *The Journal of Biological Chemistry*, vol. 276, No. 18, (May 4, 2001), pp. 15275-15283.
Robert J. Turner et al., *The Journal of Biological Chemistry*, vol. 275, No. 36, (Sep. 8, 2000), pp. 27681-27688.
Lesley A. Stark et al., *Journal of Virology*, vol. 72, No. 4, (Apr. 1998), pp. 3037-3044.
Yannick Grosskreutz et al., *Biol. Chem.*, vol. 382, (Oct. 2001), pp. 1455-1462.
Nathalie Griffon et al., *The EMBO Journal*, vol. 18, No. 17, (1999), pp. 4711-4721.
Shan Cen et al., *Journal of Virology*, vol. 75, No. 11, (Jun. 2001), pp. 5043-5048.
Pierre Fechter et al., *Journal of Molecular Biology*, vol. 309, (2001), pp. 387-399.
Valerie Guez et al., *Biochemistry*, vol. 39, (2000), pp. 1739-1747.
Keisuke Wakasugi et al., *Science*, vol. 284, (Apr. 2, 1999), pp. 147-151.
Keisuke Wakasugi et al., *The Journal of Biological Chemistry*, vol. 274, No. 33, (Aug. 13, 1999), pp. 23155-23159.
Fumie Hamano-Takaku et al., *The Journal of Biological Chemistry*, vol. 275, No. 51, (Dec. 22, 2000), pp. 40324-40328.
Satoshi Ohno et al., *The Journal of Biochemistry*, vol. 130, (2001), pp. 417-423.
J.C. Salazar et al., *FEBS Letters*, vol. 491, (2001), pp. 257-260.
Feng Xu, et al., *Nucleic Acids Research*, vol. 29, No. 20, (2001), pp. 4125-4133.
Sunghoon Kim et al., *FEBS Letters*, vol. 427, (1998), pp. 259-262.
Nobukazu Shimada et al., *The Journal of Biological Chemistry*, vol. 276, No. 50, (Dec. 14, 2001), pp. 46770-46778.
George Simos et al., *The EMBO Journal*, vol. 15, No. 19, (1996), pp. 5437-5448.
Sang Won Lee et al., *Gene*, vol. 215, (1998), pp. 311-318.
B. Menand et al., *Proc. Natl. Acad. Sci.*, vol. 95, (Sep. 1998), pp. 11014-11019.
James Williams et al., *Nucleic Acids Research*, vol. 23, No. 8, (1995), pp. 1307-1310.
Valerie Lamour et al., *Proc. Natl. Acad. Sci.*, vol. 91, (Aug. 1994), pp. 8670-8674.
Yu Pavlov et al.; J. Mol. Biol.; vol. 273; 1997; pp. 389-401.
Koichi Ito et al.; Proc. Natl. Acad. Sci.; vol. 95; Jul. 1998; pates 8165-8169.
Randall et al., Proc. Natl. Acad. Sci. USA vol. 94, 1997, pp. 802-807.

\* cited by examiner

Fig. 5 A
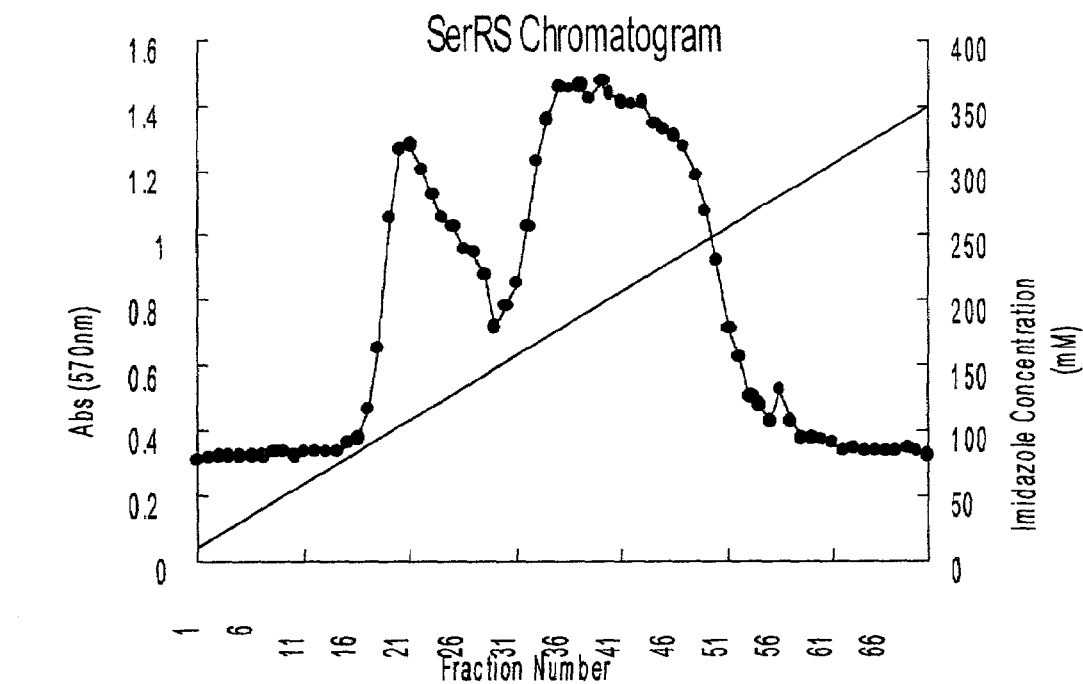
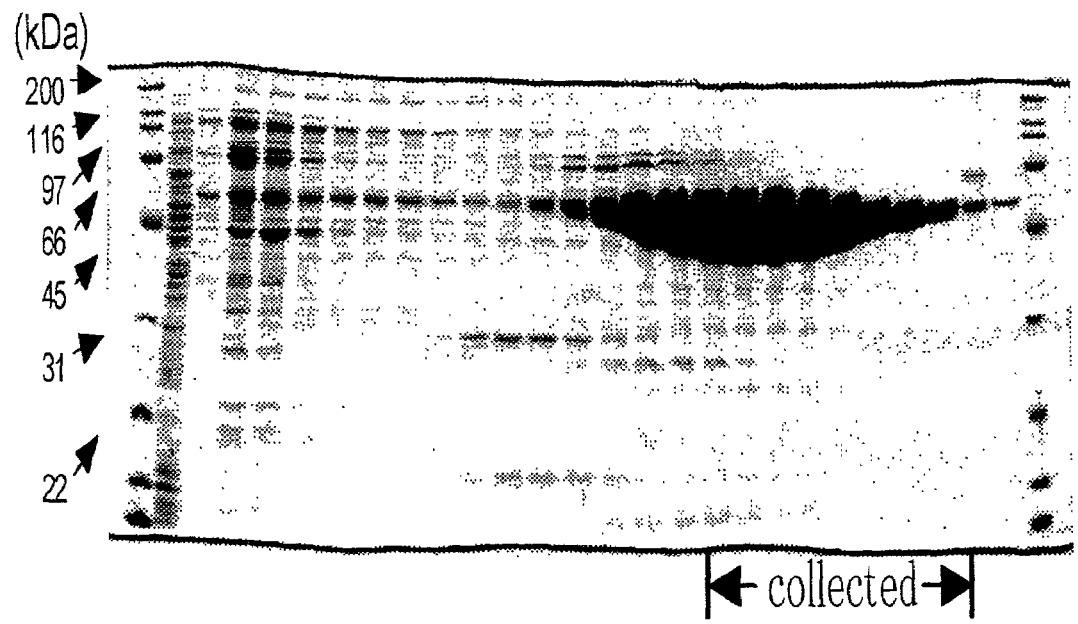
Fig. 5 B

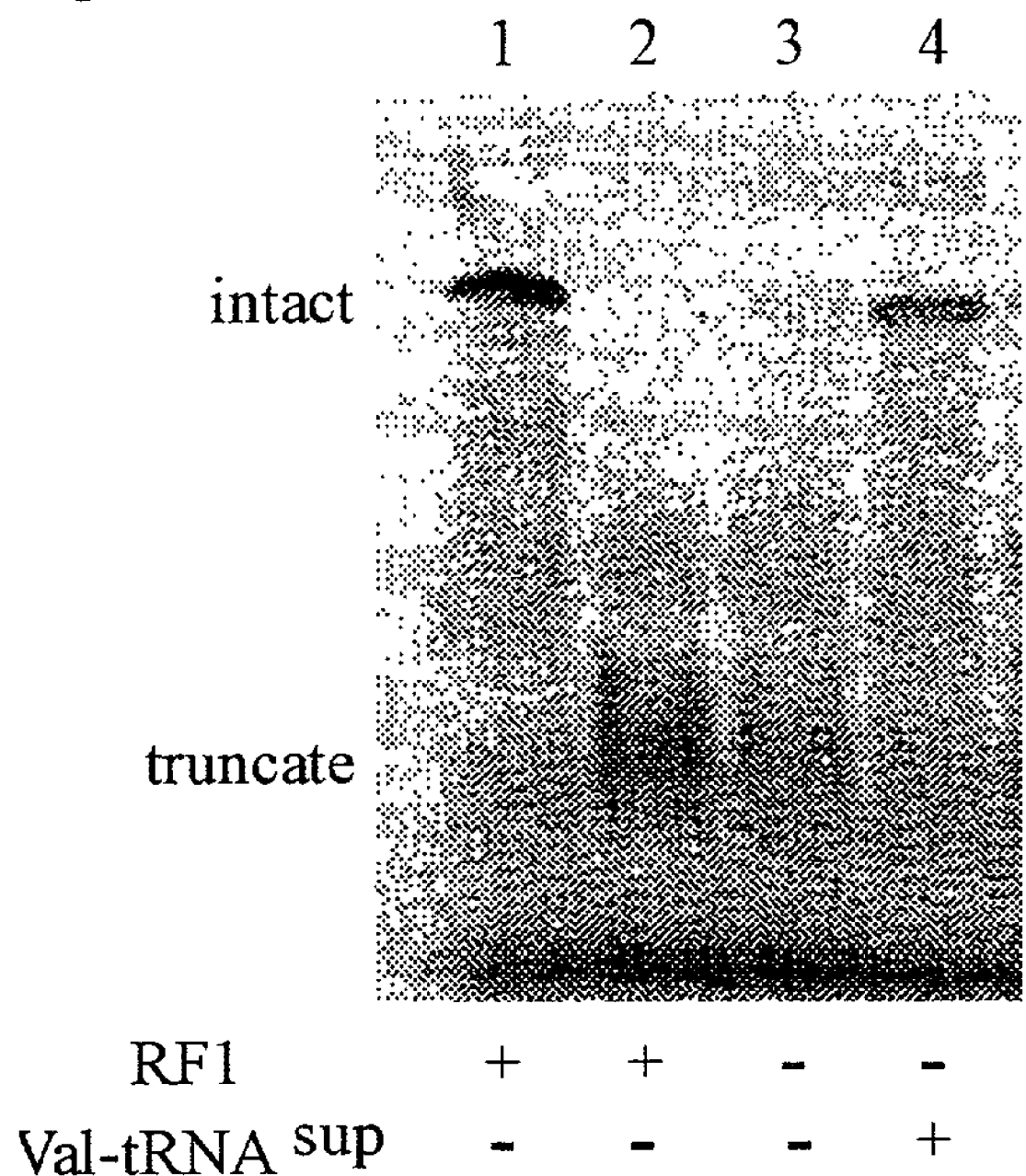

SEQUENCE LISTING

<160> NUMBER OF SEQ ID NOS: 6

<210> SEQ ID NO 1
<211> LENGTH: 14
<212> TYPE: PRT

<213> ORGANISM: Bovine sp.

<400> SEQUENCE: 1

Ser Asn Lys Glu Gln Glu Pro Lys Glu Lys Lys Lys Lys
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Strep-tag binding to streptavidin
<221> NAME/KEY: MISC_FEATURE
<222> LOCATION: (1)..(9)
<223> OTHER INFORMATION: Schmidt & Skerra, 1993, "The random peptide
      library-assisted enginerring of a C-terminal affinity peptide,
      useful for the detection and purification of a functional IgFv
      fragment", Protein Eng. 6(1):109-122.

<400> SEQUENCE: 2

Ala Trp Arg His Pro Gln Phe Gly Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Strep-tag II used in the binding of
      streptavidin
<221> NAME/KEY: MISC_FEATURE
<222> LOCATION: (1)..(9)
<223> OTHER INFORMATION: Schmidt et al., 1996, "Molecular interaction
      between the Strep-tag affinity peptide and its cognate target,
      streptavidin", J. of Mol. Biol. 255(5):753-766.

<400> SEQUENCE: 3

Asn Trp Ser His Pro Gln Phe Glu Lys
1               5

<210> SEQ ID NO 4
<211> LENGTH: 12
<212> TYPE: RNA
<213> ORGANISM: Artificial Sequence
<220> FEATURE:
<223> OTHER INFORMATION: RNA sequence to obtain a template for MFL mRNA
<221> NAME/KEY: mRNA
<222> LOCATION: (1)..(12)
<223> OTHER INFORMATION:

<400> SEQUENCE: 4
auguucuugu aa                                                              12

<210> SEQ ID NO 5
<211> LENGTH: 14
<212> TYPE: DNA
<213> ORGANISM: Artificial Sequence
<220> FEATURE:
<223> OTHER INFORMATION: oligonucleotide A that anneals to SEQ ID NO: 6
      to give a double-stranded DNA containing NdeI and XhoI sequences

<400> SEQUENCE: 5
tatgttcttg taac                                                            14

<210> SEQ ID NO 6
<211> LENGTH: 16
<212> TYPE: DNA
<213> ORGANISM: Artificial Sequence
<220> FEATURE:

-continued

```
<223> OTHER INFORMATION: oligonucleotide B that anneals to SEQ ID NO: 5
      to give a double-stranded DNA containing NdeI and XhoI sequences

<400> SEQUENCE: 6
tcgagttaca agaaca                                                      16
```

PROCESS FOR PRODUCING PEPTIDES BY USING IN VITRO TRANSCRIPTION/TRANSLATION SYSTEM

BACKGROUND OF THE INVENTION

1. Technical Field to which the Invention Belongs

This invention relates to a process for producing a peptide or a peptide derivative by using a reaction system of transcribing a DNA into an RNA and then translating the RNA produced or a reaction system of translating an RNA in vitro (hereinafter referred to as "in vitro transcription/translation reaction system") and a kit of protein components which comprises enzymes and factors for the constitution of this reaction system.

2. Description of the Related Art

There have been known cell-free protein synthesis systems derived from *Escherichia coli*, rabbit reticulocytes, or wheat germ (Current Opinion in Biotechnology 9:534–548 (1998), J. Biotechnology 41:81–90 (1995)). In these cell-free systems, peptides can be synthesized within several hours. Namely, proteins can be synthesized within a short time compared with the case where foreign genes are inserted into host cells and then expressed therein (Proc. Natl. Acad. Sci. USA 94:412–417 (1997), FEBS Letters 414:268–270 (1997)). Moreover, it is recognized or expected that synthesis of proteins in cell-free systems has a number of technical advantages, at least theoretically, over the case of inserting foreign gene into host cells and expressing the same. Namely, use of these cell-free protein synthesis systems makes it possible to produce peptides which would be digested by proteases originating in host cells and peptides showing toxicity on host cells. It is also possible by using these systems to produce peptide derivatives which do not occur in nature by incorporating unnatural amino acid residues into specific positions by using aminoacyl-tRNA charged by the unnatural amino acid residues (Annu. Rev. Biophys. Biomol. Struct. 24:435–462 (1995)), or complexes (polysome displays) composed of mRNA, ribosome and peptide. These polysome displays and utilization thereof are reported by He M. et al., J. Immunological Methods 231 (2000) pp. 105–117, Schaffitzel C., J. Immunological Methods231 (2000) pp. 119–135, Roberts R W., Current Opinion in Chemical Biology 3 (1999) pp. 268–273 and ibid. 9 (1998) pp. 534–548 (in particular, on and after p. 543) and, in addition, described in, e.g., FEBS Lett. 450:105–110 (1999), Proc. Natl. Acad. Sci. USA 95:14130–14135 (1998), and Proc. Natl. Acad. Sci. USA 94:4937–4942 (1997).

Although crude cell extracts per se were employed at the early stage, only unstable reactions could be performed thereby and thus peptides were synthesized only at low yield, namely, from 0.1 to 0.01% of vital cells. Subsequent studies have clarified components contained in extracts which are necessary for gene expression and simultaneously revealed that unnecessary components and inhibitors (for example endogenous nuclease degrading mRNA (RNA 6:1079–1090 (2000)) are contained therein. Thus attempts have been made to eliminate these unnecessary components. However, the conventional method, which comprises using a cell-free extract as a base and eliminating unnecessary components therefrom, suffers from problems that reaction energy is consumed and thus the reaction stops in about 1 hour in protein synthesis when using a batch system. It is pointed out that factors causative of these problems include starvation of nucleotide triphosphates (Biochim. Biophys. Acta. 1293:207–212 (1996), J. Biotechnol. 48:1–8 (1996)), accumulation of small by-products such as triphosphate hydrolyzates formed by endogenous enzymes (Biochemistry 22:346–354 (1983), J. Biol. Chem. 260:15585–15591 (1985)) and energy consumption by factors unnecessary for the transcription/translation reaction (J. Ferment. Bioeng. 84:7–13 (1997), J. Biotechnol. 61:199–208 (1998)).

The problem of the termination of reaction within a short time can be avoided by continuously supplying a substrate in a transcription/translation reaction system for synthesizing a peptide. However, there arises another problem of poor reproducibility in this case too. This problem has been solved by clarifying the presence of a germ ribosome inactivator (tritin) and a translation initiation inhibitor in studies on a system using wheat germ and employing a means of eliminating these substances from germ (Bio Industry Vol. 17, No.5, 20–27 (2000)). However, there still remains another problem that such a system consumes massive energy source wastefully irrespective of translation.

It was considered that these problems encountering in the conventional methods were caused by the presence of various unknown components in cell extracts which were unnecessary in the transcription or translation reaction but could be hardly eliminated completely. From this viewpoint, an attempt was made to synthesize a peptide in vitro by exclusively using enzymes and factors essentially required in the translation (The Journal of Biological Chemistry Vol. 252, No.19, 6889–6894 (1997)). For the DNA-directed synthesis of β-galactosidase in this case, use was exclusively made of, in addition to *E. coli* ribosomes, the following 33 components purified from *E. coli* extract as factors and enzymes for the transcription and translation: RNA polymerase, $N^{10}$-formyltetrahydrofolate Met-tRNA$^f$ transformylase, 20 aminoacyl-tRNA synthetases, IF-1, IF-2, IF-3, EF-Tu, EF-G, RF-1 and/or RF-2, CRP, L and $L_\alpha$. In this study, however, the target product could be obtained only in a trace amount since only poor information about the translation mechanism and insufficient purification techniques were available in those days.

Subsequently, Gonza and his co-workers constructed an in vitro peptide synthesis system from pre-charged aminoacyl-tRNAs (i.e., having activated amino acid attached thereto) and purified translation factors (Biochem. Biophys. Res. Commun. 126:792–798 (1985)). On the other hand, Pavlov and co-workers reconstructed an in vitro translation system using a partially purified aminoacyl-tRNA synthetase mixture with purified translation factors (Archives of Biochemistry and Biophysics Vol. 328, No. 1, 9–16 (1996)). They also constructed a completely purified in vitro translation system using short artificial mRNA (J. Mol. Biol. 273:389–401 (1997)). However, it has never been reported so far as the inventors know that a protein is successfully synthesized from natural mRNA by using a translation system exclusively comprising essential enzymes and factors. In the conventional cell-free peptide synthesis systems and in vitro peptide synthesis systems using cell extracts, moreover, troublesome procedures are needed for isolating and purifying a target peptide product from protein components in the reaction system and, therefore, the target peptide can be obtained only at a poor yield.

SUMMARY OF THE INVENTION

The present invention aims at constructing an efficient protein synthesis system whereby the problem of energy consumption in systems for synthesizing peptides in vitro can be overcome, and providing an in vitro peptide synthesis system whereby a peptide product can be efficiently isolated from the reaction system at a high purity.

The present invention relates to a process for producing a peptide or a peptide derivative by using a reaction system of transcribing a DNA into an RNA and then translating the RNA produced or a reaction system of translating an RNA in vitro wherein a part or all of protein components constituting the transcription/translation reaction system are labeled with one of a pair of substances adhering to each other and the other substance is used as an adsorbent for capturing said labeled protein components after translating. In this process, a plural number of combinations of said first and second substances used for labeling a part or all of the protein components constituting the reaction system with the substance used as an adsorbent for capturing the labeled protein components may be used in the transcription/translation reaction system.

The protein components labeled with a first substance or a second substance adhering to each other are a part or all of factors and enzymes for the transcription or translation reaction. Particular examples of these factors and enzymes include initiation factors, elongation factors, termination factors, aminoacyl-tRNA synthetase, methionyl-tRNA transformylase and RNA polymerase.

The protein components labeled with a first substance or a second substance adhering to each other are the factors and enzymes for the transcription or translation reaction and other enzymes required in the constitution of the reaction system. Examples of the enzymes required in the constitution of the reaction system other than the factors and enzymes for the transcription or translation reaction include enzymes for regenerating energy in the reaction system and enzymes for hydrolyzing inorganic pyrophosphoric acid formed during the transcription or translation reaction.

According to the present invention, unnatural peptides carrying unnatural amino acid residues incorporated into desired positions and peptide derivatives such as polysome displays can be produced by using the reaction system for transcribing a DNA into an RNA and then translating the RNA produced or translating an RNA in vitro which is free from termination factors.

In the present invention, the combination of first and second substances, i.e., mutually interacting in affinity chromatography can be selected from among a combination of a protein or a peptide fragment with a metal ion, a combination of an antigen with an antibody, a combination of a protein with a protein or a peptide fragment, a combination a of protein with a specific low-molecular weight compound selected from the group consisting of amino acids, DNAs, dyes, vitamins and lectins, a combination of a protein with a saccharide and a combination of a protein or a peptide fragment with an ion exchange resin. Among all, it is favorable to use a combination of histidine tag with a metal chelate such as a nickel complex or a cobalt complex taking advantage of a bond between a protein or a peptide fragment and a metal ion.

The first and second substances adhering to each other usable in the present invention are not restricted to a combination of substances mutually interacting in affinity chromatography. Use may be made therefor of, for example, substances magnetically adhering to each other too.

The present invention further relates to a kit of protein components for a reaction system for producing a peptide or a peptide derivative by transcribing a DNA into an RNA and then translating the RNA produced or translating an RNA in vitro wherein the kit comprises a part or all of protein components constituting the transcription/translation reaction system and that the protein components are selected from the group consisting of enzymes and factors which are labeled with one of a pair of substances adhering to each other. In this kit, the protein components are selected from the factors and enzymes for the transcription or translation reaction and other enzymes required in the constitution of the reaction system. Particular examples of the factors and enzymes for the transcription or translation reaction include initiation factors, elongation factors, termination factors, aminoacyl-tRNA synthetase, methionyl-tRNA transformylase and RNA polymerase. Particular examples of the enzymes required in the constitution of the reaction system other than the factors and enzymes for the transcription or translation reaction include enzymes for regenerating energy in the reaction system and enzymes for hydrolyzing inorganic pyrophosphoric acid formed during the transcription or translation reaction. The kit of protein components according to the present invention may comprise an adsorbent for capturing the protein components labeled with one of a pair of the substances adhering to each other.

The kit of protein components according to the present invention may comprise combinations, different from each other, of the first and second substances, wherein the first substance is used for labeling a part or all of the protein components constituting the reaction system and the second substance is used as an adsorbent for capturing the protein components labeled by the first substance.

The in vitro synthesis system of the present invention is a reaction system for synthesizing a peptide by transcribing a DNA into an RNA and then translating the RNA produced or translating an RNA without using cells per se. The term "peptide" as used herein means a substance composed of 2 or more natural or unnatural amino acids attached to each other via peptide bond and involves oligopeptides and polypeptides in its scope. Moreover, proteins having a specific three-dimensional structure of polypeptides fall within this category. The term "RNA" as used herein involves synthetic RNAs and mRNAs in its category, while the term "DNA" as used herein involves synthetic DNAs and cDNAs in its category.

The in vitro synthesis system of the present invention, wherein a DNA is transcribed into an RNA and then the RNA produced is translated or an RNA is translated, is a reaction system existing in prokaryotic cells or eukaryotic cells and consisting of ribosome, factors and enzymes for the transcription or translation reaction, other enzymes required in the constitution of the reaction system, various substrates, buffers and salts. Although the excellent effects of the present invention can be established in a reaction system having been completely reconstituted artificially, the present invention is also applicable to reaction systems wherein some of these constituents are added in the form of a cell extract.

The factors and enzymes for the transcription or translation reaction are not restricted to those originating in prokaryotic cells such as *E. coli* but use can be made of those originating in eukaryotic cells. In case (1) of translating an RNA, these factors and enzymes include initiation factors, elongation factors, termination factors, 20 aminoacyl-tRNA synthetases, and tRNAs attached to natural or unnatural amino acids, and methionyl-tRNA transformuylase is further included in an *E. coil-origin* in vitro reaction system. In case (2) of transcribing a DNA into an RNA and then translating the RNA produced, these factors and enzymes include, in addition to those cited in the above case (1), RNA polymerase such as T7RNA polymerase. The translation reaction can be regulated by eliminating the termination factors from the reaction system of the above-described case (1) or (2), as will be discussed hereinafter.

Examples of the enzymes other than the factors and enzymes for the transcription or translation reaction include enzymes for regenerating energy in the reaction system such as creatine kinase, myokinase and nucleoside diphosphate kinase (NDK), and enzymes for hydrolyzing inorganic pyrophosphoric acid formed during the transcription or translation reaction such as inorganic pyrophosphatase.

Examples of the various substrates include natural amino acids, unnatural amino acids, nucleotide triphosphates as an energy source, creatine phosphate and formylfolic acid. Nucleotide triphosphates include ATP, GTP, CTP and UTP. ATP and GTP are used in the above-described case (1), while ATP, GTP, CTP and UTP are used in the above-described case (2).

As the buffer, potassium phosphate buffer (pH 7.3) is usually employed. As the salts, use is usually made of, for example, potassium glutamate, ammonium chloride, magnesium acetate, calcium chloride, putrecine, spermidine and dithiothreitol (DTT). Needless to say, adequate components other than those cited above can be employed too in the reaction system.

The first characteristic of the present invention resides in that, in a system for synthesizing a peptide by transcribing a DNA into an RNA and then translating the RNA produced or translating an RNA in vitro, apart or all of protein components constituting the transcription/translation reaction system are labeled with one of a pair of substances adhering to each other and the other substance is used as an adsorbent for capturing said labeled protein components after translating. Thus, the target peptide can be easily separated from the protein components constituting the reaction system and obtained at an extremely high purity.

Histidine-tagging has been sometimes employed in producing and purifying individual protein components constituting a reaction system, in particular, factors and enzymes for transcription/translation reaction. For example, it is reported to use histidine-tag in, for example, the production and purification of elongation factors EF-Tu (Eur. J. Biochem. 210:177–183 (1992)), EF-G (Cell 92: 131–139 (1998)) and EF-Ts (Archives of Biochemistry and Biophysics 348:157–162 (1997)), the production and purification of a termination factor RF2 (Proc. Natl. Acad. Sci. USA 95:8165–8169 (1998)), and the production and purification of phenylalanyl-tRNA synthetase (Protein Expression and Purification 8: 347–357 (1996)). In these cases, however, the production and purification were carried not to construct an in vitro peptide synthesis system but merely to examine the functions or properties of individual proteins.

To separate a protein or a protein derivative produced by expressing a gene in a transformant, such as *E. coli*, affinity chromatography with the use of, for example, a combination of histidine tag with a nickel column, a combination of glutathione S-transferase with a glutathione-Sepharose resin column or a combination of an epitope tag with an antibody has been used. In such a case, it has been a practice to incorporate a residue capable of selectively binding to the adsorption column into the target peptide. In cell-free systems with the use of marketed cell extracts, use is made of a vector for incorporating histidine tag into a target peptide. In such a case, therefore, the product is obtained in the form of a fused protein of the target peptide with the histidine tag which should be enzymatically cut off from the peptide after synthesizing.

On the contrary to these conventional methods, the present inventors have introduced one of a pair of first and second substances adhering to each other not into the target peptide but protein components constituting the in vitro peptide synthesis system, based on a novel finding that the transcription or translation reaction can proceed even though the factors and enzymes for the transcription or translation and other enzymes are labeled with one of a pair of the substances adhering to each other.

The combination of a pair of the first and second substances adhering to each other to be used in the present invention may be an arbitrary one, so long as the transcription or translation reaction is not disturbed thereby. Although the adhesion of these substances to each other may be either reversible or irreversible, it is preferable to use a pair of substances which reversibly adhere to each other. This is because the protein components constituting the reaction system can be repeatedly used in such a case.

As an example of the combination of the first and second substances adhering to each other, citation may be made of a combination of an adsorption column with a substance capable of selectively binding to the adsorption column. Typical examples thereof include substances mutually interacting in affinity chromatography. For example, a metal complex such as a nickel or cobalt complex serves as a ligand of an adsorption column while histidine tag serves as a substance capable of selectively binding to the adsorption column. Moreover, use can be made of combinations of various ligands with substances capable of selectively binding thereto as will be discussed hereinafter, so long as the reaction is not disturbed thereby. That is to say, the combination of the first and second substances mutually interacting in affinity chromatography usable in the present invention can be selected from among, for example, a combination of a protein or a peptide fragment with a metal ion, a combination of an antigen with an antibody, a combination of a protein with a protein or a peptide fragment, a combination of a protein with a specific low-molecular weight compound selected from the group consisting of amino acids, DNAs, dyes, vitamins and lectins, a combination of a protein with a saccharide and a combination of a protein or a peptide fragment with an ion exchange resin.

The first and second substances adhering to each other usable in the present invention are not restricted to a combination of substances mutually interacting in affinity chromatography but can be arbitrarily selected depending on the purpose. For example, use may be made therefor of substances magnetically adhering to each other. As an example thereof, a combination of a magnetic bead-labeled protein with a magnet may be cited. In this case, protein components constituting the peptide synthesis system, which have been individually labeled with the magnetic beads, can be adsorbed by the magnet and thus captured.

In the present invention, the adsorbent (i.e., the second substance) is used in the form of, for example, a column, a matrix, a filter or a bead. Alternatively, it may be fixed to a carrier (support), if desired. To fix the adsorbent to the carrier, an appropriate means can be selected from among known techniques depending on the properties of the adsorbent.

There are a plural number of combinations of the first substance for labeling a part or all of the protein components constituting the reaction system with the second substance used as the adsorbent for capturing the protein components thus labeled by the first substance. It is possible to use such combinations differing from each other in a single reaction system. It may be rather considered as favorable to select the most suitable labels for respective protein components and then select adsorbents appropriate for these labels.

Since the factors and enzymes for the transcription/translation reaction system and other enzymes are labeled with one of a pair of the first and second substances adhering to each other in the present invention, the protein components constituting the reaction system can be obtained each in a highly pure state and the reaction system is not contaminated with any unknown and unnecessary or inhibitory components. Thus, the reaction system can be established and, consequently, the reaction efficiency can be largely elevated. In addition, it becomes possible to quickly separate the target peptide from these reaction constituents after synthesizing the peptide. In the conventional cell-free systems, a peptide formed by the reaction is purified by extraction. It is therefore needed to select an appropriate purification procedure in each case depending on the physical and chemical properties of the reaction product. In the present invention, in contrast thereto, the components constituting the reaction system are eliminated by using the adsorbent (i.e., the second substance) and the reaction product is thus purified. Accordingly, it is theoretically possible to apply the same purification procedure to any reaction products regardless of the physical and chemical properties thereof. In addition, the target peptide thus obtained has a very high purity.

According to the present invention, furthermore, the components of the reaction system can be surely controlled, which makes it possible to establish a reaction system free from termination factors. Owing to this characteristic, the present invention enables the construction of polysome displays of various types, thereby broadening the application range of the in vitro peptide synthesis systems. More particularly speaking, ternary complexes (polysome displays) composed of peptide, RNA and ribosome can be obtained by expressing various DNAs or RNAs in the termination factor-free in vitro peptide synthesis system according to the present invention. By separating such a polysome display from other complexes with the use of the peptide as a target, the target peptide and RNA can be obtained at the same time. By treating the product with termination factors, the corresponding RNA can be obtained. In this case, the peptide, which has been cut off from the ribosome, and RNA corresponding to it can be easily isolated by treating with termination factors labeled with one of a pair of the substances adhering to each other. For example, a corresponding DNA can be obtained from an isolated polysome display by using the RT-PCR method, as described in Current Opinion in Biotechnology 9:534–548 (1998). By decomposing this polysome display with EDTA, an RNA can be obtained. In particular, it is technically advantageous that an RNA or a DNA corresponding to a selected target peptide can be easily obtained in random expression. Although semirandom expression of DNAs and RNAs in a cell-free system with the use of a rabbit reticulocyte kit is already known, complicated procedures are needed in this case (WO91/05058).

By surely controlling the components constituting the reaction system, it becomes possible to synthesize a peptide having an unnatural amino acid residue by the in vitro peptide synthesis system. Namely, a peptide having an unnatural amino acid residue can be synthesized by using the production process according to the present invention as follows. A suppressor tRNA charged by an unnatural amino acid residue and corresponding to a termination codon differing from the C-terminal termination codon is added to the reaction system. Then a DNA or an RNA, which has been modified by inserting a termination codon corresponding to the suppressor tRNA into a position for the incorporation of an unnatural amino acid residue, is transcribed or translated to thereby give a peptide having the unnatural amino acid residue incorporated thereinto. Speaking in greater detail, the synthesis can be carried out as follows. To incorporate the unnatural amino acid residue, one of termination codons (UAA, UAG and UGA) such as UGA or UAG is inserted into a desired position within the open reading frame (ORF) and UAA is employed for terminating the translation. Subsequently, a suppressor tRNA carrying an anticodon to UGA and/or UAG is formed by in vitro transcription and charged by the unnatural amino acid. Then the production process according to the present invention is performed by using this RNA and suppressor tRNA as described above to translate the RNA. Thus, a peptide having the unnatural amino acid residue site-specifically inserted therein can be synthesized. Alternatively, the peptide can be synthesized by separately synthesizing the corresponding DNA followed by transcription and translation.

Use of a reaction system obtained by eliminating termination factors from the above-described reaction system makes it possible to obtain a polysome display composed of peptide, mRNA and ribosome which carries one or more unnatural amino acid residues at desired position(s). By treating this polysome display with termination factors labeled with one of a pair of substances adhering to each others as in the above case, the peptide, which has been cut off from the ribosome, and the RNA corresponding to it can be easily isolated. For example, a corresponding DNA can be obtained from a polysome display by using the RT-PCR method as described in Current Opinion in Biotechnology 9:534–548 (1998). By decomposing this polysome display with EDTA, it is also possible to obtain the RNA.

Accordingly, the peptide derivatives produced by the process of the present invention involve polysome displays and unnatural peptides having unnatural amino acid residues at desired positions.

The process for producing a peptide or a peptide derivative according to the present invention can be performed by using a batch system in a conventional manner. Alternatively, it may be carried out by using various already known or usual methods such as a flow method, wherein materials including the substrates are continuously supplied or the reaction product is occasionally withdrawn, or a dialysis method (see, for example, Japanese patent publication 110236/1995, Tanpakushitsu, Kakusan, Koso (Proteins, Nucleic acids and Enzymes) Vol. 44, No. 4, 598–605 (1999), Current Opinion in Biotechnology 9:534–548 (1998)).

Next, the present invention will be illustrated in greater detail by reference to the following examples. However, it should be understood that the invention is not construed as being restricted thereto.

(1) Peptides and Peptide Derivatives which can be produced by the Invention

According to the production process of the present invention, natural peptides and unnatural peptides of any types can be produced. That is to say, use of the process of the present invention makes it possible to produce peptides which would be digested by proteases originating in host cells such as dihydrofolate reductase (DHFR), lysozyme (originating in λ-phage) and green fluorescent proteins (GFPs), and peptides showing toxicity on host cells. The term "natural peptides" as used herein means peptides composed of 20 natural amino acids used in genetic codes, while peptides containing other α-amino acids are called "unnatural peptides".

Moreover, ternary complexes (polysome displays) composed of peptide, RNA and ribosome can be easily obtained by using a termination factor-free reaction system in the production process of the present invention.

Examples of unnatural peptides which can be produced by the process according to the present invention include peptides having modified natural amino acids, modified non-charged amino acids, modified acidic amino acids, modified basic amino acids, non-α-amino acids, amino acids with φ,φ-angle displacement, and amino acids having functional groups selected from the group consisting of nitro, amidine, hydroxylamine, quinone, aliphatic compounds, and cyclic and unsaturated hydrocarbyl groups. There have been already known processes for synthesizing these peptides in cell-free protein synthesis systems with the use of cell extracts (see, for example, JP-W-Hei-4-504651/WO90/05785). As a particular example of these unnatural peptides, DHFR having a protected cysteine residue inserted into an appropriate position, which would not occur in nature, may be cited. Further citation may be made of peptides having an unnatural amino acid residue such as p-fluorophenylalanine, p-nitrophenylalanine or homophenylalanine incorporated into a desired position. It is already known that β-lactamase variants having these 3 unnatural amino acid residues incorporated as a substitute for phenylalanine at the 66-position show sufficient enzyme activity (Bio Industry 8:749–759 (991)). These unnatural peptides can be easily produced by the process according to the present invention too.

(2) Ribosome

Ribosome is a particle where peptides are synthesized. It binds to mRNA and coordinates aminoacyl-tRNA to the A-position and formylmethionyl-tRNA or peptidyl-tRNA to the P-position, thereby forming a peptide bond (Science 289:920–930 (2000)). In the present invention, any ribosome can be used regardless of the origin, so long as it has the function as described above. Although $E.$ $coli$ ribosome is usually employed, use can be made of eukaryotic ribosomes too. It is preferable in the present invention to use $E.$ $coli$ ribosome, for example, those obtained from $E.$ $coli$ A19 strain or MRE600 strain.

(3) Factors and Enzymes for the Transcription or Translation to be Used in the in vitro Peptide Synthesis System According to the Present Invention (3-1) Initiation Factors Initiation factors means factors which are essentially required in the formation of an initiation complex in the process of peptide synthesis or remarkably promote it. IF1, IF2 and IF3 are known as initiation factors originating in $E.$ $coli$ (Biochemistry 29:5881–5889 (1990)). IF3 promotes the dissociation of ribosome into 30S and 50S subunits (i.e., the step required for initiating translation) and hinders the insertion of tRNAs other than formylmethionyl-tRNA into the P-position in the step of forming the initiation complex. IF2 binds to formylmethionyl-tRNA and transfers the formylmethionyl-tRNA to the P-position of 30S subunit, thereby forming the initiation complex. IF1 potentiates the functions of IF2 and IF3. In the present invention, it is preferable to use $E.$ $coli$-origin initiation factors, for example, those obtained from $E.$ $coli$ K12 strain. However, it is also possible to use eukaryotic initiation factors.

(3-2) Elongation Factors

An elongation factor EF-Tu is classified into 2 types, i.e., GTP and GDP types. EF-Tu of the GTP type binds to aminoacyl-tRNA and transfers it to the A-position of ribosome. When EF-Tu is released from ribosome, GTP is hydrolyzed into GDP (EMBO J. 17:7490–7497 (1998)). Another elongation factor EF-Ts binds to EF-Tu of the GDP type and promotes the conversion of it into the GTP type (Archives of Biochemistry and Biophysics 348:157–162 (1997)). Another elongation factor EF-G promotes translocation following the peptide bond formation in the process of peptide chain elongation (Nature Structural Biology 6:643–647 (1999), FEMS Microbiology Reviews 23:317–333 (1999)) In the present invention, it is preferable to use $E.$ $coli$-origin elongation factors, for example, those obtained from $E.$ $coli$ K12 strain. However, it is also possible to use eukaryotic elongation factors.

(3-3) Termination Factors

Termination factors are essentially required in terminating protein synthesis, releasing the translated peptide chain and recycling ribosome for the initiation of the subsequent mRNA translation. When a protein is synthesized in a termination factor-free reaction system, the reaction stops before the termination codon and thus a stable ternary complex (polysome display) composed of ribosome, peptide and mRNA can be easily formed. An unnatural amino acid is incorporated into a peptide chain by eliminating either RF1 or RF2 from the reaction system. That is to say, an unnatural amino acid is incorporated at a high efficiency into the UAG codon in case of eliminating RF1 or into the UGA codon in case of eliminating RF2.

When a termination codon (UAA, UAG or UGA) is located at the A-position of ribosome, termination factors RF1 and RF2 enter the A-position and promote the dissociation of the peptide chain from peptidyl-tRNA at the P-position. RF1 recognizes UAA and UAG among the termination codons, while RF2 recognizes UAA and UGA. Another termination factor RF3 promotes the dissociation of RF1 and RF2 from ribosome after the dissociation of the peptide chain by RF1 and RF2. Ribosome recycling factor (RRF) promotes the dissociation of tRNA remaining at the P-position after the protein synthesis and the recycling of ribosome for the subsequent protein synthesis. In the present invention, RRF is referred to as one of termination factors. The functions of these termination factors RF1, RF2, RF3 and RRF are described in EMBO J. 16:4126–4133 (1997) and EMBO J. 16:4134–4141 (1997). In the present invention, it is preferable to use $E.$ $coli$-origin termination factors, for example, those obtained from $E.$ $coli$ K12 strain. However, it is also possible to use eukaryotic termination factors.

(3-4) Aminoacyl-tRNA Synthetase

Aminoacyl-tRNA synthetase is an enzyme by which an amino acid is covalently bonded to tRNA in the presence of ATP to thereby synthesize aminoacyl-tRNA (RNA 3:954–960 (1997), Tanpakushitsu, Kakusan, Koso (Proteins, Nucleic Acids and Enzymes) 39: 1215–1225 (1994)). In the present invention, it is preferable to use $E.$ $coli$-origin aminoacyl-tRNA synthetase, for example, one obtained from $E.$ $coli$ K12 strain. However, it is also possible to use eukaryotic aminoacyl-tRNA synthetases.

(3-5) Methionyl-tRNA Transformylase

N-Formylmethionine (fMet) carrying a formyl group attached to the amino group at the end of methionine serves as the initiation amino acid in a prokaryotic protein synthesis system. This formyl group is attached to the methionine in methionyl-tRNA by methionyl-tRNA transformylase (MTF). Namely, methionyl-tRNA transformylase transfers the formyl group in $N^{10}$-formyltetrahydrofolate to the N-terminus of methionyl-tRNA corresponding to the initiation codon, thereby giving formylmethionyl-tRNA (Proc. Natl. Acad. Sci. USA 96:875–880 (1999)). The formyl group thus attached is recognized by IF2 and thus acts as an initiation signal for protein synthesis. Although MTF does not occur in the synthesis system in eukaryotic cytoplasm, it is present in the synthesis systems in eukaryotic mitochondria and chloroplast. In the present invention, it is preferable to use E. coli-origin methionyl-tRNA transformylase, for example, one obtained from E. coli K12 strain.

(3-6) RNA Polymerase

It is known that RNA polymerase, which is an enzyme transcribing a DNA sequence into an RNA, occurs in various organisms. As an example thereof, citation may be made of T7RNA polymerase originating in T7 phage which is an enzyme binding to a specific DNA sequence called T7 promoter and then transcribing the downstream DNA sequence into an RNA. The present inventors attached His-tag to the N-terminus of this T7RNA polymerase and expressed it as a fused protein in a large amount in E. coli BL21 strain. Then, they purified the expression product by affinity chromatography with the use of a nickel column. The His-tagged T7RNA polymerase thus obtained is a novel one. In addition to T7RNA polymerase, various RNA polymerases are usable in the present invention. For example, commercially available T3RNA polymerase and SP6RNA polymerase can be used.

(3-7) Aminoacyl-tRNA Attached to Unnatural Amino Acid

By incorporating amino acid residues, other than 20 amino acids constituting natural proteins, into proteins, it is possible to improve the functions inherent to the proteins or to impart new useful functions or characteristics to the proteins. Aminoacyl-tRNA attached to an unnatural amino acid can be produced by synthesizing a 3'-terminal CA-deficient suppressor tRNA via in vitro transcription and ligating it to chemically synthesized aminoacyl-pCpA having the unnatural amino acid by using RNA ligase (Baiosaiensu to Indasutori (Bioscience and Industry) 47:16–24 (1989)).

(4) Enzymes Required in the Constitution of the Reaction System Other Than the Factors and Enzymes for the Transcription or Translation to be Used in the In Vitro Peptide Synthesis System According to the Present Invention (4-1) Enzymes for Regenerating Energy in the Reaction System Examples of the enzymes of this type include creatine kinase, myokinase and nucleoside diphosphate kinase (NDK). Creatine kinase, which is also called creatine phosphokinase (CPK), catalyzes transfer of phosphate group from ATP to creatin. Myokinase, which is also called adenylate kinase, participates in the regeneration of ATP from ADP and the simultaneous formation of AMP. NDK catalyzes γ-phosphate group transfer between nucleoside diphosphate and nucleoside triphosphate. In the present invention, it is preferable to use these enzymes originating in E. coli, for example, those obtained from E. coli K12 strain. However, it is also possible to use eukaryotic enzymes.

(4-2) Enzymes for Hydrolyzing Inorganic Pyrophosphoric Acid Formed During the Transcription or Translation Reaction As an example of the enzymes of this type, inorganic pyrophosphatase may be cited. In the present invention, it is preferable to use E. coli-origin enzymes, for example, those obtained from E. coli K12 strain. However, it is also possible to use eukaryotic enzymes.

Among the constituents of the reaction system as described in the above (3) and (4), protein components are expressed in a large amount in E. coli (for example, commercially available E. coli BL21 strain) in the form of fused proteins (for example, His-tagged proteins) labeled at the N- or C-terminus with one of a pair of the first and second substances adhering to each other as will be described in greater detail hereinafter. Then these proteins thus expressed are purified by using an adsorbent such as a nickel column containing the other substance such as fast protein liquid chromatography (FPLC) and then supplied to the reaction system. In addition to E. coli, it is possible to express these proteins in animal cells, yeasts, Bacillus subtilis or the like. Alternatively, it is possible to produce these proteins by using an in vitro peptide synthesis system.

(5) Label and Adsorbent, i.e., a Pair of First and Second Substances Adhering to Each Other In the present invention, all or a part of the protein components constituting the reaction system as described in the above (3) and (4) are labeled with one of a pair of substances adhering to each other and the thus labeled protein components are captured by using the other substance as an adsorbent to thereby isolate the target peptide formed in the reaction system. As typical examples of a pair of the first and second substances adhering to each other, substances mutually interacting in affinity chromatography can be cited. However, any pair of first and second substances adhering to each other are usable in the present invention without restriction to substances mutually interacting in affinity chromatography, so long as these substances can be used in capturing the protein components.

Proteins exert physiological effects via specific mutual interactions with certain substances. Adsorption chromatography which is carried out by taking advantage of such a specific interaction (affinity) between a protein and a certain substance (ligand) is called affinity chromatography. Examples of a combination of the first and second substances adhering specifically to each other include a protein or a peptide fragment with a metal ion or a chelate compound, an antigen with an antibody, a cytokine or a hormone with a receptor, and an enzyme with a substrate or an inhibitor. Furthermore, specific amino acids, DNAs, dyes, vitamins, lectins and the like mutually bind to proteins having affinities therefor respectively.

One of the substances of such a combination is fixed as a ligand to a carrier or a support to form an adsorbent. Then materials labeled with the other substance (the protein components constituting the reaction system in the case of the present invention) are passed therethrough. Thus, the label (the first substance) specifically binds to the ligand (the second substance). Affinity chromatography based on this specific binding has been commonly employed as a means of purifying proteins. Various carriers have been marketed by a number of manufacturers, which makes this means highly available. In purifying a protein using an antigen-antibody reaction, for example, use is made of a combination of an antigen determinant (an epitope) having a known structure with an antibody specific to the epitope. There have been marketed various combinations of vectors and adsorbents for carrying out this means. In a preferred embodiment of the present invention, use is made of a combination of such substances adsorbing to each other which are employed in affinity chromatography. In preparing the labeled protein components to be used in the present invention, the label is useful in the purification. It is also possible to label the protein components with a plural number of labels at the same time. In this case, it is possible that the label usable for the purification in the production process is cut off while other labels are used for the separation of the target product formed in the in vitro peptide synthesis system.

Now, embodiments of the present invention will be illustrated by citing some examples of the combination of the first and second substances adhering to each other. However, it is to be understood that the present invention is not construed as being restricted these examples.

(5-1) Process With the Use of Binding of Protein or Peptide Fragment to Metal Ion or Chelate Compound A. His Tag With Metal Complex Such as Nickel Complex or Cobalt Complex It has been a practice to purify a protein by using the binding of His tag to a metal complex such as a nickel complex or a cobalt complex. Namely, His tag is attached to a DNA to be expressed to give a fused protein having His tag. Then this fused protein is captured and purified by using a column having, for example, a nickel complex, cobalt complex, a copper complex or a zinc complex. Then the protein can be eluted from the column with an eluent containing imidazole (see, for example, Tanpakushitsu Jikken Noto (Protein Experiment Note) (I), on and after p. 139, Chap. 5:1. His-Tag Tanpakusthitu no Hatugen to Seisei (Expression and Purification of His-Tag Protein), Yasumitsu and Wakui, published by Yodosha; J. A. Bornhorst and J. J. Falke, Purification of Proteins Using Polyhistidine Affinity Tags. Methods in Enzymology 326:245–254, (2000); Proteins 41:144–53 (2000), FEMS Microbiol. Lett. 188:147–51 (2000); and J. Bacteriol. 182: 4304–9 (2000)). These combinations are usable in the present invention.

To express genes encoding His-tagged protein components, it is known to use, for example, *E. coli* (M. W. Van Dyke, M. Sirito, and M. Sawadogo, Gene 111:95, 1992), *Saccharomyces cerevisiae* (D. C. Kaslow and J. Shiloach, Bio/Technology 12:494, 1994), mammalian cells (R. Janknecht and A. Nordheim, Gene 121:321, 1992), and baculovirus-infected insect cells (A. Kuusinen, M. Arvola, C. Oker-Blom, and K. Keinanen, Eur. J. Biochem. 233:720, 1995). These cells may be optionally used in the present invention.

The following protocol roughly shows an example of the process of the purification of a His-tagged protein component by using His tag and a nickel column. There have been known a number of variations of this process and an appropriate one may be selected therefrom.

1. Attach a His tag consisting of 6 His residues to the N-terminus of a target protein by a genetic engineering technique to thereby give a fused protein.
2. Disrupt cells expressing the tagged protein by sonication on ice and suspend the disrupted cells in loading buffer (300 mM NaCl, 50 mM $NaH_2PO_4$, pH 8.0).
3. Centrifuge the cell lysate (30,000 g, 4° C., 30 min)
4. Add 50% $Ni^{2+}$-NTA slurry (Qiagen) pre-equilibrated in ice-cold loading buffer to the supernatant. Stir at 4° C. for 1 hr.
5. Load the resin onto a column. Wash the column with 20 column volumes of loading buffer at 4° C.
6. Wash the column with 20 column volumes of loading buffer (containing 10 mM imidazole, pH 8.0) at 4° C.
7. Elute the target protein with a 20 column volumes of loading buffer under an imidazole concentration gradient of 10 to 250 mM in the loading buffer. Collect 1 ml fractions and identify the target protein by SDS-PAGE.

B. Thioredoxin with Phenylarsine Oxide (PAO)

In this process, a fused protein composed of a target protein with thioredoxin is formed and adsorbed by a PAO-fixed agarose gel (ThioBond™ resin, Invitrogen) by taking advantage of binding of thioredoxin to PAO followed by elution with β-mercaptoethanol (β-ME) (A. Alejo, R. J. Yanez, J. M. Rodriguez, E. Vinuela, and M. L. Salas, African Swine Fever Virus trans-Prenyltransferase, The Journal of Biological Chemistry 272: 9417–9423, 1997). This process is also usable in the present invention.

The following protocol roughly shows an example of the process of the purification of a protein by using this process.

1. Dilute overnight culture of transformed cells (*E. coli*/ vector pTrxFus, Invitrogen) 20-fold in RM medium (0.6% $Na_2HPO_4$, 0.3% $KH_2PO_4$, 0.05% NaCl, 0.1% $NH_4Cl$, 2% casamino acids, 0.0095% $MgCl_2$) containing 100 μg/ml (final concentration) of ampicillin and incubate at 30° C.
2. After incubating to $A_{550}$=0.5, add 100 μg/ml (the final concentration) of tryptophan to induce the expression of the fused protein. Then continue the incubation at 34° C. for additional 2 hr.
3. Harvest the cells by centrifugation. Suspend the cell pellet in 5 ml of running buffer [100 mM Tris-HCl (pH 7), 150 mM NaCl, 1 mM EDTA, 1 mM β-mercaptoethanol]. Then disrupt the cells by sonication.
4. Centrifuge the cell suspension (10,000 g, 15 min) and collect the supernatant.
5. Incubate the supernatant with 2 ml of ThioBond™ resin at 4° C. for 60 min to bond the fused protein contained in the supernatant to the resin.
6. Pack a column with the slurry and wash with 30 column volumes of running buffer [100 mM Tris-HCl (pH 7), 150 mM NaCl, 1 mM EDTA, 20 mM β-mercaptoethanol].
7. Elute the target protein with the running buffer under a β-mercaptoethanol gradient.

(5-2) Process With the Use of Binding of Antigen or Antigen Fragment (Epitope Tag) to Antibody A. T7-tag and Monoclonal Antibody Specific to T7-tag T7-Tag is a sequence consisting of 11 amino acids of gene 10 originating in phage T7. A combination of T7-tag with an antibody against it is employed in a means of purifying protein. Namely, this process comprises attaching a DNA sequence encoding T7-tag to a gene, then expressing the target protein, and capturing and purifying the T7-tagged fused protein thus obtained by using a monoclonal antibody specific to T7-tag as an adsorbent. As an example of the adsorbent, T7-Tag Antibody Agarose is marketed (Novagen). Citric acid is used as an eluent. This combination is also usable in the present invention. See R. Deora, T. Tseng, and T. K. Misra, Alternative Transcription Factor $\sigma^{SB}$ of *Staphylococcus aureus:* Characterization and Role in Transcription of the Global Regulatory Locus sar. Journal of Bacteriology 179:6355–6359, 1997.

The following protocol roughly shows an example of the process of the purification of a T7-tagged protein component. There have been known a number of variations of this process and an appropriate one may be selected therefrom.

1. Grow transformed cells *E. coli*/vector pET (Novagen) in 2xYT medium (1.6% Bacto Trypton, 1% yeast extract, 0.5% NaCl, 0.4% glucose) containing 20 μg/ml of chloramphenicol and 30 μg/ml of kanamycin.
2. After incubating to $A_{600}$=0.6, add IPTG to induce the expression of the target protein. Then continue the incubation for additional 2 hr.
3. Harvest the cells by centrifugation. Suspend the cell pellet in 10 ml ice-cold T7-Tag bind/wash buffer (4.29 mM Na$_2$HPO$_4$, 1.47 mM KH$_2$PO$_4$, 2.7 MM KCl, 137 mM NaCl, 1% Tween-20, 0.02% sodium azide (pH 7.3)).
4. Disrupt the cells by sonication on ice until the suspension shows no viscosity any more.
5. Centrifuge (39,000 g, 20 min) to eliminate cell debris. Filter the supernatant through a 0.45 µm filter membrane.
6. Apply the cell extract into a T7-Tag Antibody Agarose column (Novagen) pre-equilibrated with T7-Tag bind/wash buffer. Wash the column with the same buffer to eliminate nonspecifically bonded proteins.
7. Elute the target protein with elution buffer (0.1 M citric acid (pH 2.2)).

B. Process of Using Binding of FLAG Peptide Tag™ (Sigma) to Anti-FLAG Antibody™ (Sigma)

FLAG peptide tag™ (Sigma, and so on), which is a peptide consisting of 8 amino acids, is used in purifying proteins as a so-called epitope tag together with an antibody against it. Namely, a protein having the FLAG peptide tag at the N-terminus is constructed and captured by a FLAG antibody column. FLAG peptide is used in elution. See P. J. Woodring and J. C. Garrison, Expression, Purification, and Regulation of Two Isoforms of the Inositol 1,4,5-Trisphosphate 3-Kinase. The Journal of Biological Chemistry 272: 30447–30454, 1997.

The following protocol roughly shows an example of this process which may be appropriately modified.
1. Collect cells (host: B31 cell (Rat-1 fibroblast cell line), vector: pDouble-Trouble (pDT) mammalian expression vector) showing the expression of the target protein by centrifugation and homogenize in 8 ml of hypotonic lysis buffer containing protease inhibitors (10 µg/ml calpain inhibitors I and II, 100 µg/ml Pefabloc, 2.5 µg/ml leupeptin, 2 µg/ml aprotinin, 2 µg/ml bacitracin, 20 µg/ml benzamidine).
2. Centrifuge (2,000 g) to eliminate cell debris and nucleic acids and collect the supernatant.
3. Further centrifuge and apply the cell extract thus obtained to 1 ml of a FLAG antibody column. Wash the column with 35 ml of TBSC (50 mM Tris-HCl (pH 7.4), 150 mM NaCl, 0.1% (v/v) CHAPS).
4. Elute the target protein with 5 ml of TBSC containing 200 µg/ml of the FLAG peptide.

C. Protein A and IgG

In this process, use is made of the binding of Staphylocolcal Protein A (SPA) to antibody IgG thereof. A fused protein composed of a target protein with SPA is captured by using an IgG Sepharose column. Buffer with a low pH value is used in elution. See B. Nilsson and L. Abrahmsen, Fusion to Staphylococcal Protein A. Methods in Enzymology 185: 144–161, 1990.

The following protocol roughly shows an example of this process which may be appropriately modified.
1. Add overnight culture of transformed cells (host: *E. coli* or *S. aureus*, vector: pRIT 20 or pRIT30 series) to 25 ml of LB medium (LB medium+0.1%(w/v) glucose, 250 mg/l ampicillin) and incubate at 37° C. for 4 hr.
2. Harvest the cells by centrifugation (10,000 g, 5° C., 20 min) and filter the supernatant through a 0.45 µm filter membrane.
3. Apply the filtrate to 5 ml of an IgG Sepharose column pre-equilibrated with TST (50 mM Tris-HCl (pH 7.4), 150 mM NaCl, 0.05% (v/v) Tween 20).
4. Wash the column successively with 15 ml aliquots of TST twice and 5 ml of 1 mM ammonium acetate.
5. Elute the protein with 1 ml of 0.5 M ammonium acetate (pH 3.3).

D. Protein and Monoclonal Antibody

There is known a method of purifying cyclic nucleotide-gated (CNG) channel, which is a protein originating in bovine retina, by using a monoclonal antibody PMc 6E7 (N-terminal domain of α subunit: 63-kDa polypeptide) (R. S. Molday and L. L. Molday, Purification, Characterization, and Reconstitution of Cyclic Nucleotide-Gated Channels. Methods in Enzymology 294: 246–260, 1999). Sepharose 2B (Pharmacia) carrying the monoclonal antibody fixed thereon is used as an adsorbent. To elute the target protein, use is made of 6E7 competing peptide which is a peptide competitively binding to the monoclonal antibody and having an amino acid sequence Ser- Asn- Lys- Glu- Gln- Glu- Pro- Lys- Glu- Lys- Lys- Lys- Lys- Lys (SEQ ID NO:1). This combination is also usable in the present invention.

The following protocol shows an example of the process for purifying the bovine retina-origin protein with the use of the monoclonal antibody.
1. Collect rod outer segment (ROS) fractions from a bovine retina homogenate by centrifugation under a 30 to 50% sucrose density gradient (20 mM Tris-acetate (pH 7.4), 10 mM glucose, 1 mM MgCl$_2$; 82,500 g, at 4° C. for 45 min)
2. Dilute the ROS fraction in 5 volumes of homogenizing buffer (20% (w/v) sucrose, 20 mM Tris- acetate (pH 7.4), 10 mM glucose, 1 mM MgCl$_2$) and centrifuge (20,000 g, 4° C., 20 min)
3. Re-suspend the ROS pellet in 8 ml of homogenizing buffer to give a crude ROS extract.
4. Suspend ROS in 10 volumes of hypotonic lysis buffer (10 mM HEPES- KOH (pH 7.4), 1 mM EDTA, 1 mM DTT) and centrifuge (20,000 g, 10 min).
5. Suspend the membrane pellet in the same buffer and repeatedly wash twice.
6. Suspend the pellet in 10 mM HEPES-KOH (pH 7.4).
7. Add the ROS membranes to CHAPS (3-[3-(Cholamidopropyl)dimethylammonio]-1-propane sulfonate) solubilization buffer [10 mM HEPES- KOH (pH 7.4), 10 mM CaCl$_2$, 0.15 M KCl, 18 mM CHAPS, 2 mg/ml asolectin (soybean phosphatidylcholine, type IV-S; Sigma) protease inhibitor (0.1 mM diisoprophylfluorophosphate, 5 µg/ml aproteinin, 1 µg/ml leupeptin, 2 µg/ml pepstatin or 20 µM Pefabloc SC)] and stir slowly.
8. Centrifuge (27,000 g, 4° C., 30 min) to eliminate cell debris.
9. Apply 20 ml of the solubilized ROS membrane to a Sepharose 2B column having PMc 6E7(antibody) fixed thereon. Wash with 10 volumes of CHAPS column buffer (10 mM HEPES-KOH (pH 7.4), 1 mM CaCl$_2$, 0.15 M KCl, 12 mM CHAPS, 2 mg/ml asolectin).
10. Elute the target protein with CHAPS column buffer containing 0.1 mg/ml of 6E7 competing peptide.

(5-3) Process With the Use of Binding of Protein to Protein or Peptide Fragment

A. Strep-Tag and Streptavidin

There has been known a process for affinity purification of a protein having Strept-tag which is an oligopeptide having an affinity for streptavidin (see, for example, A. Skerra and T. G. Schmidt, Use of the Strep-Tag and Streptavidin for Detection and Purification of Recombinant Proteins. Methods in Enzymology 326: 271–311(2000), BioTechniques 28: 338–344 (2000)). This combination is also usable in the present invention.

In this process with the use of the binding of Strep-tag to streptavidin, use is made as the Strep-tag, for example, Ala-Trp-Arg-His-Pro-Gln-Phe-Gly-Gly (SEQ ID NO:2) or Asn-Trp-Ser-His-Pro-Gln-Phe-Glu-Lys (Strep-tag II )(SEQ ID NO:3). A Strep-tagged protein such as DHFR (dihydrofolate reductase) is synthesized in a cell-free system. Then it is purified by adsorbing by fixed streptavidin or Strep Tactin. As an eluent, desthiobiotin is employed.

The following protocol shows an example of the process of the production of a Strep-tagged protein component with the use of Strep-tag and streptavidin. There have been known a number of variations of this process and an appropriate one may be selected therefrom.

1. Add overnight culture of transformed *E. coli* cells (using pASK-IBA vector) to 2 l of fresh LB medium (containing ampicillin at final concentration of 100 μg/ml) and incubate to $OD_{550}=0.5$ under shaking (200 rpm) at 22° C.
2. To induce gene expression, add 200 μl of 2 mg/ml anhydrotetracycline-dimethylformamide(DMF) solution. Then continue the incubation for additional 3 hr.
3. Harvest the cells by centrifuging (4,200 g, 4° C., 12 min) Suspend the cells in 20 ml of buffer P (100 mM Tris-Cl (pH 8.0), 500 mM sucrose, 1 mM $Na_2EDTA$) and incubate on ice for 30 min.
4. Eliminate spheroplast by centrifuging (27,000 g, 4° C., 15 min).
5. Dialyze the thus obtained periplasma faction against 2 l of buffer (100 mM Tris-Cl (pH 8.0), 1 mM $Na_2EDTA$) overnight.
6. Equilibrate a StrepTactin Sepharose column with buffer W. Apply the protein solution to the column by using a system provided with a peristaltic pump, an UV detector ($A_{280}$) and a fraction collecter.
7. Wash the column with buffer W until $A_{280}$ attains the base line.
8. Elute the target protein with buffer W containing 2.5 mM of desthiobiotin.

B. S-peptide and S-protein

It is known that the protein fragment of ribonuclease S (S-protein) tightly binds to its S-peptide fragment (S-peptide) reversibly. Protein can be purified with the use of this binding. Namely, an S-tagged protein (i.e., having S-peptide attached thereto) can be captured by agarose having S-protein fixed thereto. Elution is carried out by cleaving the bond between S-tag and S-protein with, for example, 3M guanidinium thiocyanate; 0.2 M potassium citrate buffer, pH 2; 3 M $MgCl_2$ (R. T. Raines, M. McCormick, T. R. V. Oosbree, R. C. Mierendorf, The S·Tag Fusion System for Protein Purification. Methods in Enzymology 326:362–376, 2000).

The following protocol roughly shows an example of this process which may be optionally modified.

1. Add 2 ml of an S-protein agarose slurry (Novagen) to an extract of cells expressing the target protein (host: bacteria, insect, mammalian, vector: pET, pBAC (Novagen) and thoroughly stir at room temperature for 30 min.
2. Centrifuge (500 g, 10 min) and eliminate the supernatant.
3. Suspend the S-protein agarose having the target protein bonded thereto in bind/wash buffer (20 mM Tris-HCl (pH 7.5), 0.15 M NaCl, 0.1% (v/v) Triton X-100).
4. After centrifuging (500 g, 10 min), discard the supernatant to thereby eliminate proteins unspecifically bonded.
5. Suspend the S-protein agarose slurry in 1.5 volumes of elution buffer (bind/wash buffer+3 M guanidinium thiocyanate, 0.2 M potassium citrate (pH 2), or 3 M $MgCl_2$).
6. Incubate at room temperature for 10 min while occasionally stirring to maintain the suspended state.
7. After centrifuging, harvest the target protein thus eluted.

C. Calmodulin-binding Protein (CBP) and Calmodulin (CaM)

In this process, protein is purified by using an interaction between calmodulin-binding protein (CBP) and calmodulin (P. Vaillancourt, Chao-Feng Zheng, D. Q. Hoang, and L. Breister, Affinity Purification of Recombinant Proteins Fused to Calmodulin or to Calmodulin-Binding Peptides. Methods in Enzymology 326: 340–362 (2000)). This combination is also usable in the present invention.

A CBP-fused protein composed of a protein component and CBP bonded thereto is prepared. Then it is purified by adsorbing by a Sepharose 4B-based CaM affinity resin or other commercially available CaM resins. In elution, use is made of EGTA capable of forming a chelate with $Ca^{2+}$.

The following protocol shows an example of the process of the preparation of a CBP-fused protein using CBP and CaM. There have been known a number of variations of this process and an appropriate one may be selected therefrom.

1. Add 20 ml of overnight culture of transformed cells (pCA series constructed on the basis of pET-11 as a vector) overnight to 1 l of LB medium containing 50 μg/ml of ampicillin or carbenicillin. Incubate to $OD_{600}=0.6\sim10$. After adding IPTG to give a final concentration of 1 mM, continue the incubation for additional 3 to 5 hr under shaking.
2. Harvest the cells by centrifuging. Suspend the cell pellet in buffer A (50 mM Tris-HCl (pH 8.0), 150 mM NaCl, 10 mM 2-mercapto-ethanol, 1 mM magnesium acetate, 1 mM imidazole, 2 mM $CaCl_2$) containing 0.2 mg/ml of lysozyme. Disrupt the cells by sonication.
3. Centrifuge the cell lysate (25,000 g, 15 min) and collect the supernatant.
4. Equilibrate 10 ml of a CaM-Sepharose resin with buffer A.
5. Mix the CaM-Sepharose resin with the cell lysate and gently stir for 1 hr. Centrifuge at a low speed and eliminate the slurry to thereby eliminate unspecifically bonded matters.
6. Wash with 40 ml of buffer A. Re-suspend in 20 to 30 ml of buffer A and then pack into a column. Wash successively with 5 column bed volumes of buffer A and buffer B (50 mM Tris-HCl (pH 8.0), 150 mM NaCl, 10 mM 2-mercapto-ethanol, 1 mM magnesium acetate, 1 mM imidazole, 0.1 mM $CaCl_2$) until $A_{280}$ of the UV detector attains the base line.
7. Elute the target protein with buffer B containing 2 mM of EGTA.

D. HSA and ABP

There has been reported a process for purifying protein by using the binding of human serum albumin (HAS) to serum albumin binding affinity handle (ABP) (T. Graslund, J. Nilsson, A. M. Lindberg, M. Uhlen, and Per-Ake Nygren, Production of a Thermostable DNA Polymerase by Site-Specific Cleavage of A Heat- Eluted Affinity Fusion Protein. Protein Expression and Purification 9: 125–132, 1997). This process comprises expressing a target protein as a fused protein with serum albumin binding affinity handle (ABP), capturing it by an HSA-Sepharose column and eluting with buffer having a low pH value. This combination is also usable in the present invention.

The following protocol roughly shows this process for protein purification.

1. Add 5 ml of overnight culture of transformed cells (host: *E. coli*, vector: pET-21a (Novagen)) to 500 ml of TSB +YE medium (30 g/l tryptic soy broth, 5 g/l yeast extract, 100 mg/l ampicillin, 34 mg/l chloramphenicol) followed by incubation under shaking to $OD_{600}$=0.8 to 1.5.
2. To induce the expression of the fused protein, add 1 mM (the final concentration) of isopropyl β-D-thiogalactoside and continue the incubation for additional 3 to 5 hours.
3. Harvest the cells by centrifuging. Suspend the cell pellet in TST (50 mM Tris-HCl (pH 8.0), 0.2 M NaCl, 0.05% Tween 20, 1 mM EDTA) and disrupt the cells by sonication.
4. Centrifuge the disrupted cell suspension (20,000 g, 30 min). Filter the supernatant thus obtained through a 1.2 μm-hydrophilic filter.
5. Apply the cell extract to an HSA-Sepharose column.
6. Elute the target protein with a 0.5 M Hac solution (pH 2.8).

(5-4) Process With the Use of Binding of Protein to Specific Low-molecular Weight Compound Such as Amino Acid, DNA, Dye, Vitamin or Lectin A. Glutathione S-transferase (GST) and Glutathione A process for purifying protein by using an interaction between GST and glutathione, which is called the GST pull down method, has been commonly performed. (see, for example, Tanpakushitsu Jikken Noto (Protein Experiment Note) (I), on and after p. 162, Chap. 5: 1. GST-Yugo Tanpakusthitu no Hatugen to Seisei (Expression and Purification of GST-fused Protein), Suetake, D. B. Smith, Generating Fusions to Glutathione S-Transferase for Protein Studies. Methods in Enzymology 326:254–270, (2000)). This combination is also usable in the present invention.

This process comprises preparing a fused protein composed of a target protein with GST and adsorbing by glutathione-agarose employed as an adsorbent. As an eluent, use is made of reduced glutathione. In case of preparing the GST-fused protein by a genetic engineering technique, it is known to use, for example, *E. coli*, *Saccharomyces cerevisiae* or *Schizosaccharomyces pombe* as the host.

The following protocol roughly shows an example of the process of the production of GST-fused protein using GST and glutathione. There have been known a number of variations of this process and an appropriate one may be selected therefrom.

1. Dilute 100 ml of overnight culture of transformed cells in 1 l of L medium containing 100 μg/ml of ampicillin followed by incubation.
2. Harvest the cells by centrifuging (5000 g). Suspend the cell pellet in 20 ml of ice-cold PBS containing a reducing agent such as 1 to 5 mM of dithiothreitol (DTT) or 0.1% of 2-mercaptoethanol.
3. Gently sonicate the suspended cells on ice so as that the suspension does not forth. Control the sonication to such a level that the solution turns into dull gray within about 5 min.
4. Add Triton X-100 to give a final concentration of 1% and centrifuge (10,000 g, 4° C., 5 min) Apply the supernatant into a 50 ml tube. Add 1 ml of pre-swollen 50% glutathione-agarose beads and, inverting occasionally, incubate at 4° C. for 30 min.
5. Collect the beads by centrifuging (500 g, 30 min) and wash with 50 ml aliquots of ice-cold PBS thrice.
6. Elute the fused protein by gently stirring the beads with an equal volume of freshly made 50 mM Tris-HCl (pH 8) at room temperature for 5 min.
7. Eliminate the supernatant by centrifuging (500 g, 30 sec), add glycerol to give a final concentration of 10% and store in aliquots at −80° C.

B. Protein and Dye-ligand

It is reported that a native protein originating in *Zymononas mobilis* shows an affinity for specific dyes such as C.I. 17908, Reactive Red 8 and C.I. Reactive Blue 187 and this protein can be purified by using this characteristic (R. K. Scopes and K. Griffiths-Smith, Use of Differential and Dye-Ligand Chromatography with Affinity Elution for Enzyme Purification: 6-Phosphogluconate Dehydratase from *Zymononas mobilis*. Analytical Biochemistry 136: 530–534, 1984). Namely, a target protein can be purified by labeling the target protein with all or a part of this protein, adsorbing by a Sepharose affinity column using the above dye as a ligand and then eluting.

The following protocol shows the process for purifying the *Z. mobilis*-origin protein.

1. Starting from a liquid culture of *Z. mobilis*, prepare a cell extract with the use of extraction buffer (20 mM K-Mes (pH 6.5), 30 mM NaCl, 5 mM $MnCl_2$, 0.5 mM ammonium ferrous sulfate, 10 mM β-mercaptoethanol).
2. Apply to the cell extract successively to a Scarlet MX-G (C.I. 17908, Reactive Red 8)-Sepharose CL-4B column (Pharamacia) and a Blue HE-G (C.I. Reactive Blue 187)-Sepharose CL-4B column.
3. Wash the columns with 100 ml of the extraction buffer.
4. Wash not the Scarlet MX-G column but exclusively the Blue-HE-G column with the extraction buffer containing 20 mM of $Na_2So_4$.
5. Elute the target protein originating in *Z. mobilis* with 20 mM DL-α-glycerophosphate.

C. Process with the Use of Binding of Biotin to Avidin

A process for purifying a protein by using the specific binding of biotin to avidin has been known for a long time (see, for example, J. D. Alche, and H. Dickinson, Affinity Chromatographic Purification of Antibodies to a Biotinylated Fusion Protein Expression in *Escherichia coli*. Protein Expression and Purification 12:138–143, 1998). This process comprises preparing a fused protein composed of biotin and a target protein by using a sequence (122 amino acids) which is biotinylated in a host (for example, *E. coli*), capturing this fused protein by a column having avidin fixed thereto (for example, SoftLink soft release avidin resin (Promega) ) and then competitively eluting with biotin. This combination is also usable in the present invention.

The following protocol roughly shows an example of the process with the use of binding of biotin to avidin.

1. To induce gene expression, add 1 mM of IPTG (the final concentration) to overnight culture of transformed cells (host: *E. coli*, vector: PinPoint Xa-2 (Promega)) and incubate for additional 5 hr. In case where the thus expressed protein is present within the cells, treat as follows.
2. Lyse the cells by adding 10 ml per gram of the cell pellet of buffer (50 mM Trin-HCl (pH 8.0), 1 mM EDTA, 50 mM NaCl, 0.1 mM PMSF, 1 mg/ml lysozyme).
3. Collect the precipitate containing the target protein by centrifuging (18,000 g, 15 min) and suspend in buffer (50 mM Tris-HCl (pH 8), 10 mM EDTA, 50 mM NaCl, 0.5% Triron X-100, 0.1 mM PMSF) followed by washing twice.

4. After centrifuging (18,000 g, 15 min), suspend the pellet thus obtained in solubilization buffer (50 mM Tris-HCl (pH 8), 10 mM EDTA, 50 mM NaCl, 0.5% Triton X-100, 0.1 mM PMSF, 6 M guanidine-HCl).

5. Apply the cell extract to 3 ml of a SoftLink soft release avidin resin (Promega) column pre-equilibrated with 30 ml of the solubilization buffer. Wash with 60 ml of the solubilization buffer.

6. Elute the biotinylated target protein with solubilization eluent containing 5 mM of biotin.

(5-5) Process with the Use of Binding of Protein to Saccharide

In this process, a protein is purified by using an interaction between a saccharide-binding protein with a saccharide. For example, it is known to use maltose-binding protein (MBP) together with amylose (D. Sachdev and J. M. Chirgwin, Fusions to Maltose-Binding Protein: Control of Folding and Solubility in Protein Purification. Methods in Enzymology 326: 312–321(2000).) Furthermore, it is expected that use can be made of the interaction between β-galactose-binding proteins such as galectin and β-galactose. These combinations are also usable in the present invention.

A. Maltose-binding Protein and Amylose

In the process wherein a fused protein of maltose-binding protein is adsorbed by a resin having amylose fixed thereto, maltose is used as an eluent. The following protocol shows an example of the production process of a fused protein of maltose-binding protein. There have been known a number of variations of this process and an appropriate one may be selected therefrom.

1. Add 2 ml of overnight culture of transformed cells (*E. coli*/vector pMAL-c2 (New England Biolabs)) to 225 ml of LBD medium containing 100 82 g/ml of ampicillin (LB medium containing 0.2% of glucose) and incubate under shaking to $OD_{600}$=0.5 at 37° C.

2. To induce gene expression, add 0.3 mM of isopropyl-β-thiogalactopyranoside (IPTG) and continue the incubation for additional 2 to 3 hr at 30° C.

3. Harvest the cells by centrifuging (6,800 g, 5 min) Suspend the cell pellet in 10 ml of column buffer (20 mM Tris (pH 7.4), 200 mM NaCl, 1 mM EDTA, 0.02% Tween 80) and frozen at −20° C. overnight.

4. Thaw the frozen cell suspension in ice-water and dilute in 10 ml of the column buffer. Disrupt the cells by sonication (intensity: 75% of the maximum level).

5. After centrifuging (20,000 g, 4° C., 15 min), dilute the supernatant with 10 ml of the column buffer (crude extract).

6. Apply the crude extract to 10 ml of an amylose resin column.

7. Wash the column several times with 20 to 30 ml aliquots of the column buffer. Then elute the target protein with the column buffer containing 10 mM of maltose.

B. Chitin and Chitin-binding Domain (CBD)

In this process, use is made of the binding of chitin to chitin-binding domain (CBD) in purifying a protein. Namely, a fused protein composed of chitin-binding protein (CBD) bonded to a target protein via intein (inducible self-cleavage activity of engineered protein splicing elements) is expressed and then adsorbed by a chitin affinity column (New England Biolabs). In elution, the bond between intein and the target protein is cleaved with a reducing agent such as DTT, β-mercaptoethanol orcystein (see, for example, Chung-Mo Park, Jae-Yoon Shim, Song-Sook Yang, Jeong-GuKang, Jeong-Il Kim, Z. Luka, and Pill-Soon Song, Chromophore—Apoprotein Interactions in Synechocystis sp. PCC6803 Phytochrome Cph1. Biochemistry 39: 6349–6356, 2000). In case of applying this process to the protein components of the present invention, the protein components are labeled with an adhesive substance other than CBD-intein too and this adhesive label is used in the separation of the protein components from the target protein formed in the in vitro synthesis system.

The following protocol roughly shows an example of this process for purifying a protein. There have been known a number of variations thereof and an appropriate one may be selected therefrom.

1. Add 3 ml of overnight culture of transformed cells (host: *E. coli*, vector: pTYB2 (New England Biolabs)) to 250 ml of RB medium (0.5% yeast extract, 1% tryptone, 0.5% NaCl, 0.2% glucose (pH 7.5) and incubate to $OD_{600}$=0.6 at 30° C.

2. To induce the expression of the fused protein, add 1 mM of IPTG (the final concentration) and continue the incubation for additional 14 to 16 hr at 20° C.

3. Harvest the cells by centrifuging (5,000 g, 5 min). Suspend the cell pellet in lysis buffer (Tris-HCl (pH 8.0), 500 mM NaCl, 0.1% Triton X-100, 1 mM EDTA) under ice-cooling. Disrupt the cells by sonication.

4. Collect the supernatant by centrifuging (100,000 g, 30 min) and filter through a 0.2 mm filter membrane.

5. Add 20 μl of 2 mM DMSO to 1.5 ml of the cell extract. Incubate on ice for 1 hr and then apply to a chitin affinity column.

6. Wash the column with buffer (20 mM Tris-HCl (pH 8.0), 150 mM NaCl, 1 mM EDTA, 0.1% TritonX-100). Incubate in buffer containing 1 mM of DTT (the final concentration) at 4° C. overnight to induce the self-cleavage of the intein. Then collect the target protein thus released.

(5-6) Process with the Use of Binding of Protein or Peptide Fragment to Ion Exchange Resin A. Poly Arg and Ion Exchange Resin In this process, protein is purified by taking advantage of the phenomenon that a Poly Arg-tagged target protein, which is charged positively, is adsorbed by a cation exchange resin (for example, an SP-TSK HPLC column). Elution is carried out by controlling the ion strength (J. C. Smith, R. B. Derbyshire, E. Cook, L. Dunthorne, J. Viney, S. J. Brewer, H. M. Sassenfeld, and L. D. Bell, Chemical Synthesis and Cloning of a Poly (Arginine)—Coding Gene Fragment Designed to Aid Polypeptide Purification. Gene 32: 321–327, 1984).

The following protocol roughly shows an example of the above-described process. There have been known a number of variations thereof and an appropriate one may be selected therefrom.

1. Add 6 ml of overnight culture of transformed cells (host: *E. coli*, vector: pWT221) to 300 ml of M9 medium containing 100 μg/ml of ampicillin and incubate to $A_{600}$=0.4 under shaking at 37° C.

2. Add an IAA solution (20 mg/ml in ethanol) to give a final concentration of 20 μg/ml.

3. Add 0.1% of Polymin P (the final concentration) and harvest the cells by centrifuging.

4. Lyse the cell pellet in buffer (40 mM Tris-acetate (pH 5.5), 5 M urea) and dialyze against the same buffer.

5. Apply 0.1 ml of the cell extract to an SP-TSK HPLC column and wash the column by the same buffer.
6. Elute the target protein into buffer (40 mM PIPES (pH 6.0), 5 M urea) under an NaCl concentration gradient (100 mM to 350 mM).

(5-7) Process with the Use of Magnetic Beads

There have been marketed magnetic beads (Dynabeads™, DYNAL, Norway) having a uniform particle size which consist of a polymer core having magnetizable substances (for example, $\gamma Fe_2O_3$ and $Fe_3O_4$) uniformly dispersed therein and a hydrophilic polymer coating. By bonding various antibodies to the surface, these beads can be bonded to cells and proteins. When brought close to a powerful magnet (MPC), magnetic beads are magnetized and thus attracted magnetically. When the magnet is removed, the beads are demagnetized and dispersed again. Owing to these characteristics, magnetic beads have been used in, for example, purifying cells and proteins. For example, it is reported that peripheral blood B lymphocytes were isolated by using magnetic polystyrene beads (DYNAL) coated with CD19 antibody (Kanegasaki, S. et al, J. Biochem. 117: 758–765(1995)). In the present invention, it is also possible to label the protein components constituting the reaction system with magnetic beads and thus magnetically eliminate from the reaction system. That is to say, such a combination of magnetic beads with a magnet also falls within the category of the substances mutually interacting according to the present invention.

BRIEF DESCRIPTION OF THE DRAWINGS

FIG. 5A shows a diagram of UV absorption at 570 nm of elute including His-tagged SerRS. FIG. 5B shows a chromatogram of His-tagged SerRS.

FIG. 11 shows the formation of DHFR carrying valine residue incorporated into the 37-position as a model of the incorporation of an unnatural amino acid in the in vitro synthesis system of the present invention.

DETAILED DESCRIPTION OF THE PREFERRED EMBODIMENTS

Now, the present invention will be illustrated in greater detail by reference to the following Examples. However, it is understood that the invention is not construed as being restricted to these examples.

EXAMPLE 1

Preparations of *E.coli* Ribosome and Extraction of S100

Figure 1:
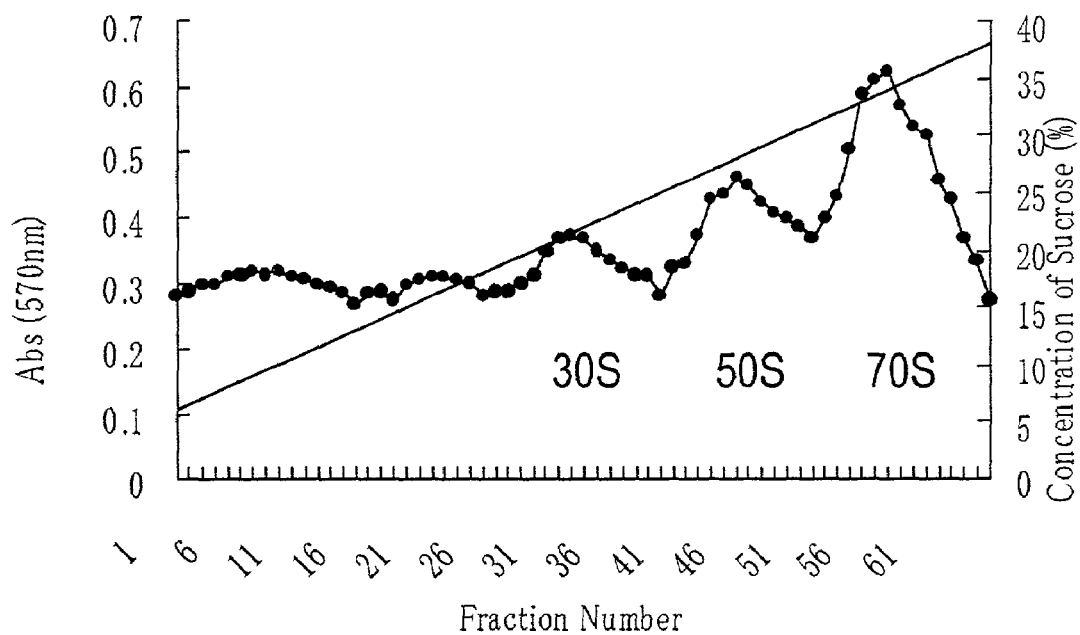
FIG. 1 shows *E. coli* ribosome fractions under a sucrose density gradient.

300 g of *E.coli* A19 cells (harvested at mid-log phase) were ground with alumina. The ground cells were suspended in buffer A (10 mM Hepes-KOH (pH7.6), 10 mM $MgCl_2$, 50 mM KCl, 1 mM DTT) and alumina and cell debris were eliminated by centrifugation at 30,000 g for 1 h at 4° C. DNase (deoxyribonuclease) was added to the resultant supernatant fraction to give a final concentration of 1 µg/ml followed by centrifugation at 100,000 g for 4 h at 4° C. The supernatant fraction thus obtained was referred to as S100. The pellet was resuspended in the buffer A and the resultant suspension was referred to as a crude ribosome extract. From this crude ribosome extract, a tight-coupled ribosome fraction was obtained under a sucrose density gradient of 6 to 36%. This tight-coupled ribosome fraction was centrifuged at 100,000 g and the pellet was suspended in ribosome buffer (20 mM Hepes-KOH (pH7.6) 6 mM MgOAc, 30 mM $NH_4Cl$ 7 mM β-mercaptoethanol) to thereby prepare tight-coupled ribosome. FIG. 1 shows the ribosome fractions under the sucrose density gradient.

EXAMPLE 2

Construction of Plasmids for Overexpressing Initiation Factors, Elongation Factors and Termination Factors Using *E. coli* A19 genome as a template, a gene sequence encoding EF-Tu gene was amplified by PCR to give a DNA fragment having an EcoRI-recognition sequence at the 5' terminus and a BglII-recognition sequence at the 3' terminus. The DNA fragment thus obtained was inserted into a plasmid pQE60 (QIAGEN) which had been cleaved with EcoRI and BglII. Thus, a vector for overexpressing EF-Tu fused with His tag at the C terminus was constructed. Next, *E. coli* BL21/pREP4 was transformed by the vector obtained above. Vectors for overexpressing other elongation factors, initiation factors and termination factors were constructed in the same manner. Table 1 summarizes the vectors and restriction enzymes employed and the His tag sites.

EXAMPLE 3

Construction of Plasmids for Overexpressing Aminoacyl-tRNA Synthetase (ARS) and Methionine-tRNA Formylase (MTF)

Using *E. coli* A19 genome as a template, a gene sequence encoding alanyl-tRNA synthetase gene was amplified by PCR to give a DNA fragment having an SphI-recognition sequence at the 5' terminus and a HindIII-recognition sequence at the 3' terminus. The DNA fragment thus obtained was inserted into a plasmid pQE30 (QIAGEN) which had been cleaved with SphI and HindIII. Thus, a vector for overexpressing alanyl-tRNA synthetase fused with His tag at the N terminus was constructed. Next, *E. coli* BL21/pREP4 was transformed by the vector obtained above. Vectors for overexpressing other ARS and MTF were constructed in the same manner. Table 1 summarizes the vectors and restriction enzymes employed and the His tag sites, wherein the plasmids obtained were transformed into *E.coli* BL21/pREP4(pQE series) or BL21/DE3(pET series) strain.

TABLE 1

| Enzymes or factors | vector | N-terminal R.E. | C-terminal R.E. | site of His-tag |
|---|---|---|---|---|
| AlaRS | pQE30 | Sph I | Hind III | N |
| ArgRS | pET16b | Nde I | Bam H I | N |
| AsnRS | pQE30 | Bam H I | Hind III | N |
| AspRS | pET21a | Nde I | Xho I | C |
| CysRS | pET21a | Nde I | Xho I | C |
| GlnRS | pET21a | Nde I | Xho I | C |
| GluRS | pET21a | Nde I | Xho I | C |
| GlyRS | pET21a | Nde I | Xho I | C |
| HisRS | pET21a | Nde I | Xho I | C |
| IleRS | pET21a | Nde I | Hind III | N |
| LeuRS | pET21a | Xba I | Xho I | C |
| LysRS | pET21a | Nde I | Xho I | C |
| MetRS | pET21a | Xba I | Xho I | C |
| PheRS | pQE30 | Sph I | Hind III | N |
| ProRS | pET21a | Nde I | Xho I | C |
| SerRS | pET21a | Xba I | Xho I | C |
| ThrRS | pQE30 | Bam H I | Hind III | N |
| TrpRS | pET21a | Nde I | Xho I | C |
| TyrRS | pET21a | Nde I | Xho I | C |
| ValRS | pET21a | Xba I | Not I | C |
| MTF | pET21a | Nde I | Xho I | C |
| IF1 | pQE30 | Bam H I | Hind III | N |
| IF2 | pQE30 | Bam H I | Hind III | N |
| IF3 | pQE30 | Bam H I | Hind III | N |
| EF-G | pQE60 | Mun I | Bgl II | C |
| EF-Tu | pQE60 | Eco R I | Bgl II | C |
| EF-Ts | pQE60 | Nco I | Bam H I | C |
| RF1 | pQE60 | Bam H I | Hind III | C |

Note: RE means a restriction enzyme.

EXAMPLE 4

Construction of Plasmid for Overexpressing T7RNA Polymerase

Using T7 phage genome as a template, a gene sequence encoding T7RNA polymerase gene was amplified by PCR to give a DNA fragment having a BamHI-recognition sequence at the 5' terminus and a PstI-recognition sequence at the 3' terminus. The DNA fragment thus obtained was inserted into a plasmid pQE30 (QIAGEN) which had been cleaved with BamHI and PstI. Thus, a vector for overexpressing T7RNA polymerase fused with His tag at the N terminus was constructed. Next, *E. coli* BL21/pREP4 was transformed by the vector obtained above.

EXAMPLE 5

Construction of Plasmids for Overexpressing Nucleoside Diphosphate Kinase (NDK) and Other Enzymes Using *E. coli* A19 genome as a template, a gene sequence encoding NDK gene was amplified by PCR to give a DNA fragment having a BamHI-recognition sequence at the 5' terminus and an HindIII-recognition sequence at the 3' terminus. The DNA fragment thus obtained was inserted into a plasmid pQE30 (QIAGEN) which had been cleaved with BamHI and HindIII. Thus, a vector for overexpressing NDK fused with His tag at the N terminus was constructed. Next, *E. coli* BL21/pREP4 was transformed by the vector obtained above. Plasmids for other enzymes exemplified in (4-1) and (4-2) at page 31 can be constructed in the same manner, if desired.

EXAMPLE 6

Figure 2:
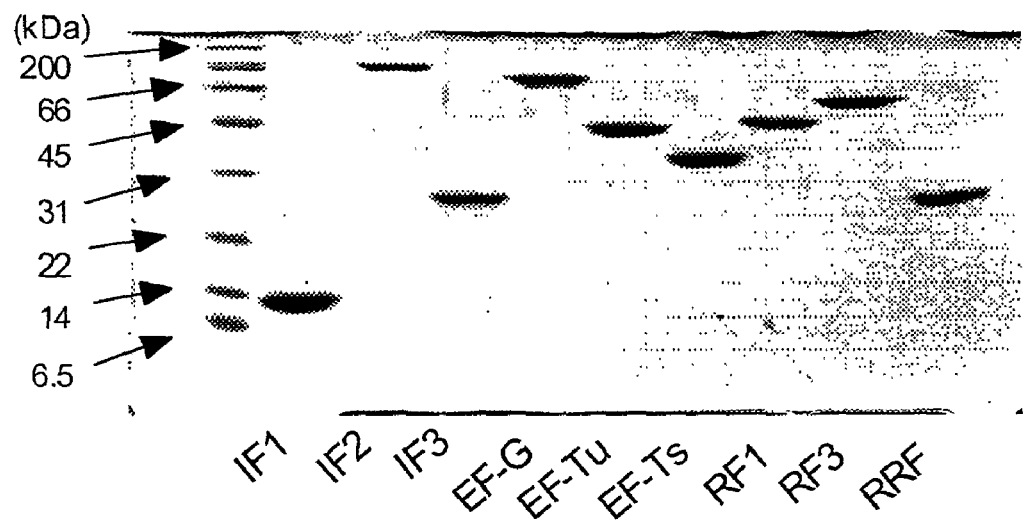
FIG. 2 shows 12% SDS-PAGE patterns of His-tagged initiation factors, elongation factors and termination factors (stained with coomassie brilliant blue).

Overexpression and Purification of Initiation Factors, Elongation Factors and Termination Factors To overexpress His-tagged EF-Tu (EF-Tu*), the transformant BL21/pREP4 cells obtained in Example 2 were grown in 6 l of LB medium until the optical density ($OD_{660}$) attained 0.7. To the culture, IPTG (isopropyl-1-thio-β-D-galactoside) was added to give a final concentration of 0.1 mM and incubation was continued for additional 4 hr at 37° C. The cells were harvested by centrifugation, resuspended in suspension buffer (50 mM Hepes-KOH (pH7.6), 1M $NH_4Cl$, 10 mM $MgCl_2$, 0.3 mg/ml lysozyme, 0.1% TritonX-100, 0.2 mM PMSF (phenylmethanesulfonyl fluoride), 6 mM β-mercaptoethanol) and disrupted by sonication. Cell debris were eliminated by centrifugation at 100,000 g for 1 hr at 4° C. The obtained supernatant was applied to an $Ni^{2+}$ pre-charged 10 ml Hi-Trap chelating column (Pharmacia) and washed with 100 ml of HT buffer (50 mM Hepes-KOH (PH7.6), 1M $NH_4Cl$, 10 mM $MgCl_2$) containing 10 mM of imidazole. Then EF-Tu* was eluted from the column under a linear gradient of imidazole concentration (10 to 400 mM) contained in the HT buffer. The EF-Tu* fractions thus purified were collected and dialyzed against stock buffer (50 mM Hepes-KOH (pH 7.6), 100 mM KCl, 10 mM $MgCl_2$, 30% glycerol). The concentration of the purified EF-Tu* was determined based on a standard curve formed by using the Bio-Rad protein assay kit using BSA (bovine serum albumin) as a standard. The obtained EF-Tu* was quickly frozen in 1 ml aliquots in liquid nitrogen and then stored at −80° C. Other His-tagged elongation factors, initiation factors and termination factors were purified in the same manner. FIG. 2 shows 12% SDS-PAGE patterns of His-tagged factors (stained with coomassie brilliant blue)

Figure 3:
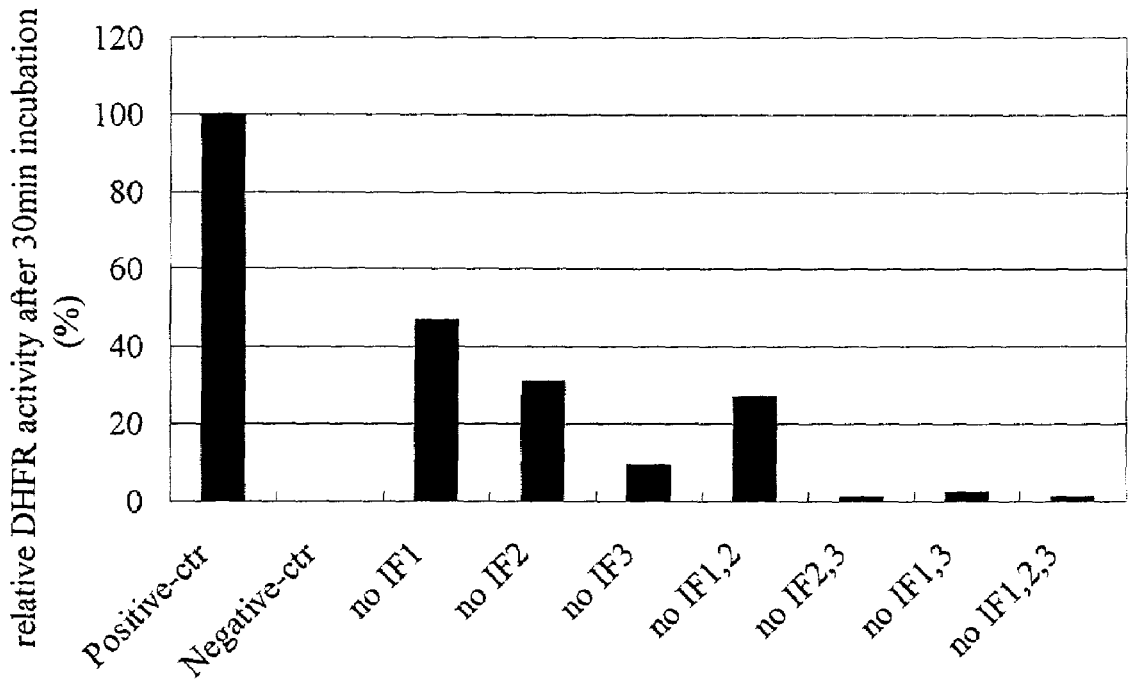
FIG. 3A shows the relative DHFR activities of His-tagged initiation factors.
FIG. 3B shows the optimum concentrations of His-tagged initiation factors expressed in the relative DHFR activities.
Figure 3:
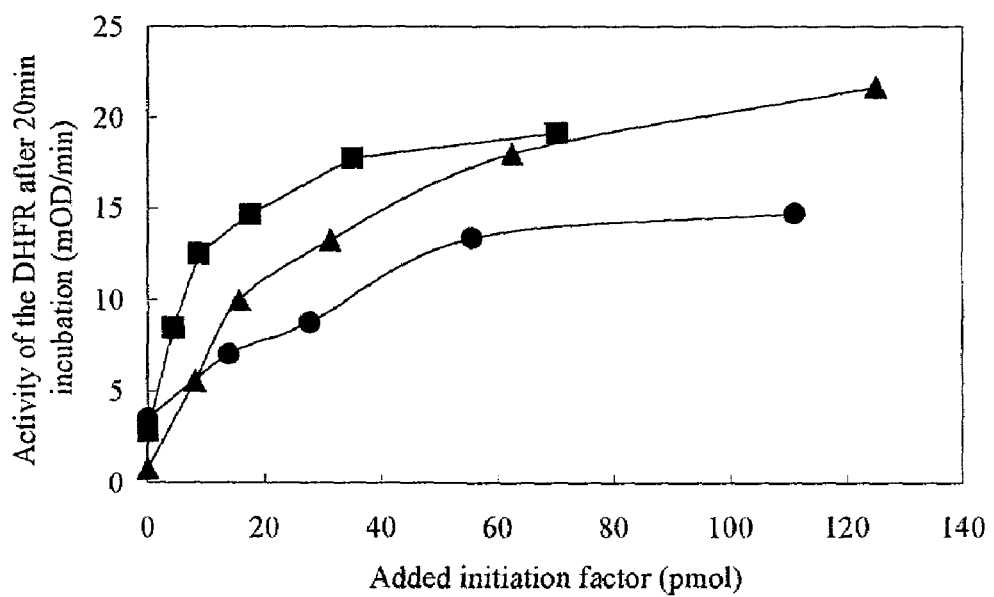

The activities and optimum concentrations of the His-tagged initiation factors (IF1, IF2 and IF3: "*" means "His-tagged") were measured with the use of a DHFR mRNA in vitro translation system (Example 17 provided hereinafter). Using a system containing all of IF1*, IF2* and IF3* as a positive control, incubation was carried out for 30 min in systems lacking respective initiation factors and then the relative activities of DHFR thus formed were compared (FIG. 3A). Namely, the activities of the His-tagged initiation factors were determined by referring the activity of the positive control as to 100. As a result, it was confirmed that the DHFR yield in each of the IF*-lacking systems corresponded to ½ or less of the positive control, which indicates that all of IF1*, IF2* and IF3* have the activity. The optimum concentrations of the His-tagged initiation factors were measured by translating in an in vitro system under constant conditions but varying the concentration of each initiation factor and measuring the relative activity of DHFR thus formed (FIG. 3B). In FIG. 3B, ●, ▲ and ■ respectively show the data of IF1*, IF2* and IF3*.

EXAMPLE 7

Overexpression and Purification of His-tagged ARSs and MTF

Transformant BL21/DE3 cells for overexpressing His-tagged Ser tRNA synthetase ("*" means "His-tagged") were grown in 2 l of LB medium until the optical density ($OD_{660}$) attained 0.7. To the culture, IPTG (isopropyl-1-thio-β-D-galactoside) was added to give a final concentration of 0.1 mM and incubation was continued for additional 4 hr at 37° C. The cells were harvested by centrifugation, resuspended in suspension buffer (50 mM Hepes-KOH (pH7.6), 1 M $NH_4Cl$, 10 mM $MgCl_2$, 0.3 mg/ml lysozyme, 0.1% Triton X-100, 0.2 mM PMSF (phenylmehtanesulfonyl fluoride), 6 mM β-mercaptoethanol) and disrupted by sonication. Cell debris were eliminated by centrifugation at 100,000 g for 1 hr at 4° C. The obtained supernatant was applied to an $Ni^{2+}$ pre-charged 10 ml Hi-Trap chelating column (Pharmacia) and washed with 100 ml of HT buffer (50 mM Hepes-KOH (PH7.6), 1 M $NH_4Cl$, 10 mM $MgCl_2$) containing 10 mM of imidazole. Then Ser tRNA synthetase* was eluted from the column under a linear gradient of imidazole concentration (10 to 400 mM) contained in the HT buffer. The Ser tRNA synthetase* fractions thus purified were collected and dialyzed against stock buffer (50 mM Hepes-KOH (pH 7.6), 100 mM KCl, 10 mM $MgCl_2$, 30% glycerol) . The concentration of the purified Ser tRNA synthetase* was determined based on a standard curve formed by using the Bio-Rad protein assay kit using BSA (bovine serum albumin) as a standard. The thus obtained Ser tRNA synthetase* was quickly frozen in 1 ml aliquots in liquid nitrogen and then stored at −80° C. FIG. 5 shows a chromatogram of the Ser tRNA synthetase* thus obtained.

Figure 6:
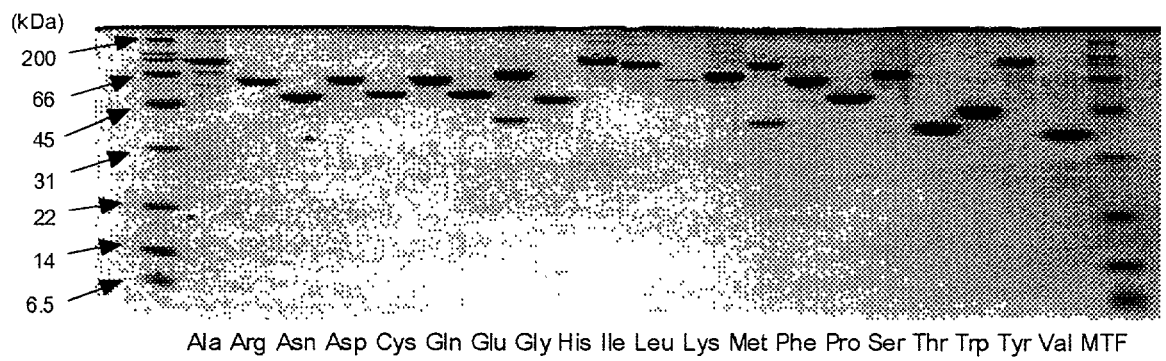
FIG. 6 shows 12% SDS-PAGE patterns of His-tagged ARSs and MTF.

Other ARS* and MTF were overexpessed and purified in the same manner. FIG. 6 shows 12% SDS-PAGE patterns of the His-tagged factors and enzymes (stained with coomassie brilliant blue) . Two bands of Gly RS* and Phe RS* observed in FIG. 6 are assignable to the fact that these enzymes have α2 and β2 types. FIG. 6 indicates that these His-tagged factors and enzymes were obtained each at a high purity.

EXAMPLE 8

Overexpression and Purification of His-tagged T7RNA Polymerase

Figure 12A:
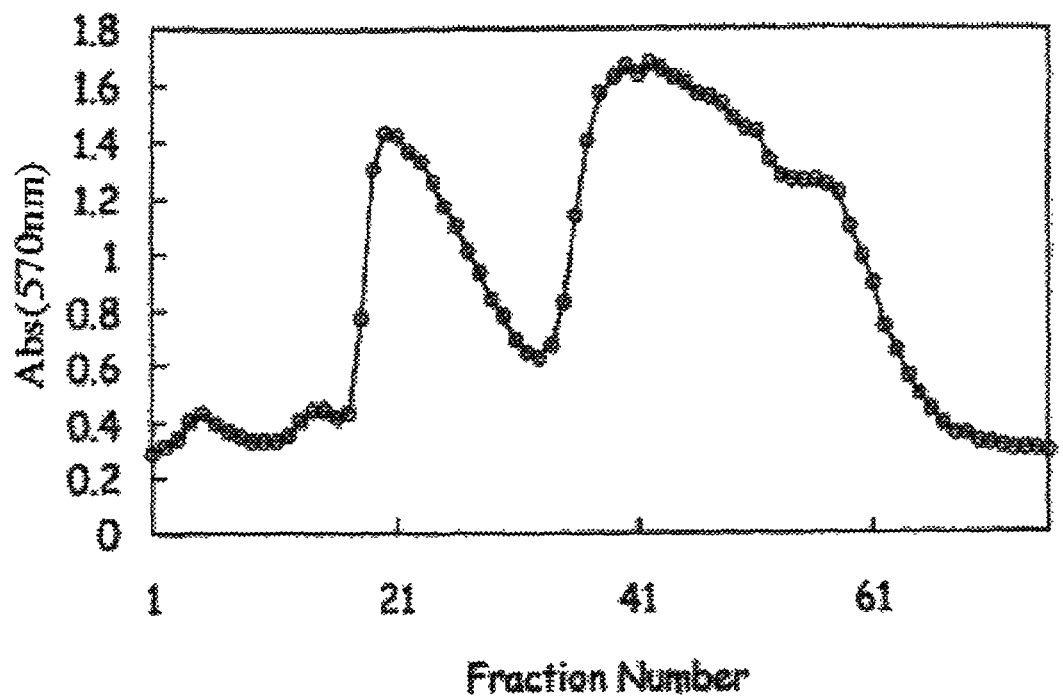
FIG. 12A shows a diagram of U absorption at 570 nm of elute including His-tagged T7RNA polymerase.
Figure 12B:
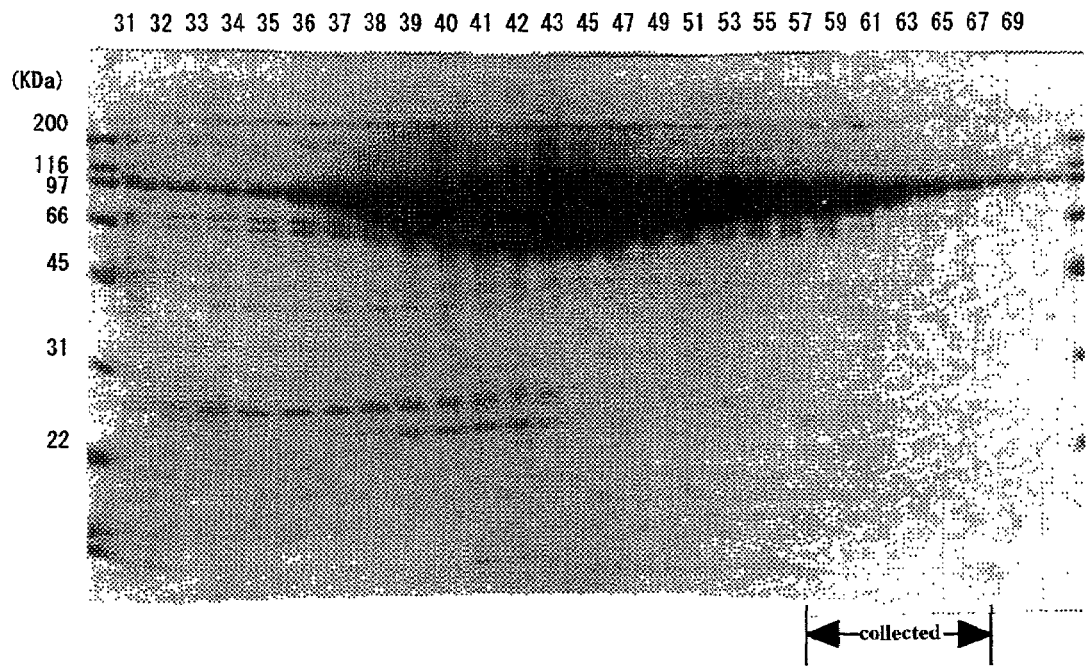
FIG. 12B shows a chromatogram of His-tagged T7RNA polymerase.

Transformant BL21/pREP4 cells for overexpressing His-tagged T7RNApolymerase ("*" means "His-tagged") were grown in 6 l of LB medium until the optical density ($OD_{660}$) attained 0.7. To the culture, IPTG (isopropyl-1-thio-β-D-galactoside) was added to give a final concentration of 0.1 mM and incubation was continued for additional 4 hr at 37° C. The cells were harvested by centrifugation, resuspended in suspension buffer (50 mM Hepes-KOH (pH7.6), 1 M $NH_4Cl$, 10 MM $MgCl_2$, 0.3mg/ml lysozyme, 0.1% TritonX-100, 0.2 mM PMSF (phenylmethanesulfonyl fluoride), 6 mM-mercaptoethanol) and disrupted by sonication. Cell debris were eliminated by centrifuging the disrupted cell suspension at 100,000 g for 1 hr at 4° C. The obtained supernatant fraction was applied to an $Ni^{2+}$ pre-charged 10 ml Hi-Trap chelating column (Pharmacia) and washed with 100 ml of HT buffer (50 mM Hepes-KOH (PH7.6), 1 M $NH_4Cl$, 10 mM $MgCl_2$) containing 10 mM of imidazole. Then T7RNA polymerase* was eluted from the column under a linear gradient of imidazole concentration (10 to 400 mM) contained in the HT buffer. The T7RNA polymerase* fractions thus purified were collected and dialyzed against stock buffer (50 mM Hepes-KOH (pH 7.6), 100 mM KCl, 10 mM $MgCl_2$, 30% glycerol) . The concentration of the purified T7RNA polymerase* was determined based on a standard curve formed by using the Bio-Rad protein assay kit using BSA (bovine serum albumin) as a standard. The obtained T7RNA polymerase* was quickly frozen in 1 ml aliquots in liquid nitrogen and then stored at −80° C. FIGS. 12A and B show chromatograms of the T7RNA polymerase* thus obtained.

EXAMPLE 9

Overexpression and Purification of His-tagged NDK and Other Enzymes

Transformant BL21/pREP4 cells for overexpressing His-tagged NDK ("*" means "His-tagged") were grown in 2 l of LB medium until the optical density ($OD_{660}$) attained 0.7. To the culture, IPTG (isopropyl-1-thio-β-D-galactoside) was added to give a final concentration of 0.1 mM and incubation was continued for additional 4 hr at 37° C.

The cells were harvested by centrifugation, resuspended in suspension buffer (50 mM Hepes-KOH (pH7.6), 1 M $NH_4Cl$, 10 mM $MgCl_2$, 0.3 mg/ml lysozyme, 0.1% Triton X-100, 0.2 mM PMSF (phenylmethanesulfonyl fluoride), 6 mM β-mercaptoethanol) and disrupted by sonication. Cell debris were eliminated by centrifugation at 100,000 g for 1 hr at 4° C. The obtained supernatant fraction was applied to an $Ni^{2+}$ pre-charged 10 ml Hi-Trap chelating column (Pharmacia) and washed with 100 ml of HT buffer (50 mM Hepes-KOH (PH7.6), 1 M $NH_4Cl$, 10 mM $MgCl_2$) containing 10 mM of imidazole. Then NDK* was eluted from the column under a linear gradient of imidazole concentration (10 to 400 mM) contained in the HT buffer. The NDK* fractions thus purified were collected and dialyzed against stock buffer (50 mM Hepes-KOH (pH7.6), 100 mM KCl, 10 mM $MgCl_2$, 30% glycerol). The concentration of the purified NDK* was determined based on a standard curve formed by using the Bio-Rad protein assay kit using BSA (bovine serum albumin) as a standard. The obtained NDK* was quickly frozen in 1 ml aliquots in liquid nitrogen and then stored at −80° C. Other His-tagged enzymes exemplified in (4-1) and (4-2) at page 31 can be obtained in the same manner, if desired.

EXAMPLE 10

Construction of DHFR Gene and Preparation of mRNA

By adding an HindIII sequence and a BamHI sequence respectively to the 5' and 3' termini, DHFR (dihydrofolate reductase) gene originating in *E.coli* was amplified by PCR. The gene contained a T7 promoter upstream of a ribosome-binding site with the "epsilon sequence" originating from bacteriophage T7 gene 10 followed by a Shine-Dalgarno (SD) sequence. This DNA fragment was cloned into a plasmid vector pUC18 (Takara Shuzo). After treating with SmaI, this plasmid was used as a template in run-off transcription or in vitro transcription coupled translation with the use of T7RNA polymerase. The an in vitro transcription reaction was carried out at 42° C. for 3 hr. The reaction mixture (1 ml) comprised 40 mM Hepes-KOH (pH 7.8), 20 mM of $MgCl_2$, 1 mM of spermidine, 5 mM of DTT, 2 mM each of ATP, UTP, CTP, and GTP, 20 μg of the SmaI-treated template plasmid, 50 μg of BSA, 1.78 units of PPiase (pyrophosphatase) and 10 μg of His-tagged T7RNA polymerase thus purified. To cease the reaction, EDTA (ethylenedinitrotetracetic acid) was added to give a final concentration of 50 mM. The mRNA thus obtained was extracted with phenol/chloroform and then precipitated with ethanol. Next, it was purified by using an RNA purification kit (QIAGEN) in accordance with the protocol recommended by the manufacturer.

EXAMPLE 11

Construction of MFL mRNA

To obtain a template for MFL mRNA, AUGUUCU-UGUAA (SEQ ID NO:4), a DNA (translated into fMet-Phe-Leu-Stop; formylmethionine-phenylalanine-leucine-stop codon; hereinafter referred to simply as MFL) was constructed as follows. An oligonucleotide A: 5'-Tatgttcttgtaac (SEQ ID NO:5) was annealed with another oligonucleotide B: 5'-TCGAgttacaagaaca (SEQ ID NO:6) to give a double-stranded DNA containing NdeI and XhoI sequences. Next, this DNA was cloned into the NdeI and XhoI sites of a plasmid vector pET29a (Novagen). The resultant plasmid was transcribed as in the above-described case of DHFR gene.

EXAMPLE 12

His-tagged Aminoacyl-tRNA Synthetase Activities

Activities of His-tagged ARSs (aminoacyl-tRNA synthetases) were measured as follows. Each reaction mixture (50 μl) comprised polymix buffer (see translation experiments) containing 1 mM of ATP, $2.8 A_{260}$ units of tRNAmix (Boehringer), 50 μM of each labeled amino acid, and each purified His-tagged ARS. Reactions were carried out at 37° C. and radioactive aminoacyl-tRNAs were precipitated on 3MM filters at different incubation times and washed with cold 5% trichloroacetic acid followed by the measurement of the radioactivity. One unit of the activity was defined as the amount of the enzyme capable of synthesizing 1 pmol of aminoacyl-tRNA per minute. Table 2 shows the results.

TABLE 2

| Enzyme | Concentration (μg/μl) | Specific activity (U/μg) | Necessary units (50 μl reaction) |
| --- | --- | --- | --- |
| AlaRS | 13 | 27 | 94 |
| ArgRS | 10 | 1300 | 130 |
| AsnRS | 30 | ND | ND |
| AspRS | 22 | 310 | 130 |
| CysRS | 25 | 500 | 31 |
| GlnRS | 36 | 330 | 63 |
| GluRS | 26 | 150 | 94 |
| GlyRS | 30 | 520 | 250 |
| HisRS | 30 | 1600 | 31 |
| IleRS | 20 | 63 | 130 |
| LeuRS | 22 | 940 | 190 |
| LysRS | 35 | 580 | 190 |
| MetRS | 27 | 3000 | 310 |
| PheRS | 23 | 15 | 63 |
| ProRS | 16 | 120 | 63 |
| SerRS | 17 | 1000 | 94 |
| ThrRS | 19 | 200 | 63 |
| TrpRS | 11 | 600 | 31 |
| TyrRS | 22 | 1800 | 31 |

TABLE 2-continued

| Enzyme | Concentration (μg/μl) | Specific activity (U/μg) | Necessary units (50 μl reaction) |
| --- | --- | --- | --- |
| ValRS | 20 | 1700 | 156 |
| MTF | 12 | 230 | 230 |

EXAMPLE 13

His-tagged Methionyl-tRNA Transformylase Activities

Activities of His-tagged MTFs were measured as follows ("A*" means "His-tagged"). Each reaction mixture (50 μl) comprised polymix buffer (see translation experiments) containing 1 mM ATP, $2.8 A_{260}$ units of tRNAmix (Boehringer), 50 μM of [$^3$H] labeled methionine, 0.5 μg of 10-formyl-5, 6,7,8,-tetrahydrofolic acid, 3000 units of MetRS, and MTF*. Reactions were carried out at 37° C. and unformylated methionyl-tRNAs were deacylated in buffer containing 0.175 M of $CuSO_4$ and 0.5 M of Tris-HCl (pH7.5) for 8 min at 30° C. Radioactive formyl-methionyl-tRNAs were precipitated on 3MM filters and washed with cold 5% trichloroacetic acid followed by the measurement of the radioactivity. One unit of activity was defined as the amount of enzyme capable of synthesizing 1 pmol of formyl-methionyl-tRNA per minute. Table 2 shows the results (the last column).

EXAMPLE 14

Translation Experiments (General Procedure)

Translation mixtures (50 μl) were prepared by slightly modifying polymix buffer employed by Jelenc et al. (1979) and Wagner et al. (1982). The polymix buffer contained 5 mM of magnesium acetate, 5 mM of potassium phosphate (pH7.3), 95 mM of potassium glutamate, 5 mM of ammonium chloride, 0.5 mM of calcium chloride, 1 mM of spermidine, 8 mM of putrescine and 1 mM of DTT. Each reaction mixture contained 1 mM of ATP, 1 mM of GTP, 10 mM of creatine phosphate, $2.8 A_{260}$ units of tRNAmix, 0.5 μg of 10-formyl-5,6,7,8,-tetrahydrophilic acid, 1 mM of each of amino acid and the factor mix as will be described hereinafter. In case of transcription coupled translation reaction, 1 mM of each NTP and 4 mM of magnesium acetate were further added to the above reaction mixture. The factor and enzyme mix comprised 12 pmol of ribosome, 1 μg of IF1*, 2 μg of IF2*, 0.75 μg of IF3*, 1 μg of EF-G*, 2 μg of EF-Tu*, 1 μg of EF-Ts*, 0.5 μg of RF1*, 0.5 μg of RF3*, 0.5 μg of RRF*, 30 to 300 units of each ARS* or MTF, 0.2 μg of creatine kinase (CK), 0.15 μg of myokinase (MK) and 0.054 μg of nucleoside diphosphate kinase* (NDK). In case of transcription coupled translation, 1.78 units of PPiase and 0.5 g of T7RNA polymerase* were further added. Among the factors and enzymes, those marked "*" mean His-tagged ones. Reaction mixtures were incubated at 37° C. for 5 min, then template DNA or RNA was added and reaction was started. Translation was carried out at 37° C. After the completion of the reaction, ribosome having high molecular weight was first eliminated by passing through a ultrafiltration membrane with a cut-off of 100 kDa. Next, the fraction having passed through the ultrafiltration membrane was applied to an Ni column and thus the His-tag fusion proteins were eliminated. The component passing through the column was the translation product having a high purity which showed a single band in SDS-PAGE. The S30 system employed in the following experiments was purchased from Promega and translation was carried out in accordance with to the protocol recommended by the manufacturer.

EXAMPLE 15

Expression of Various Proteins

Figure 13:
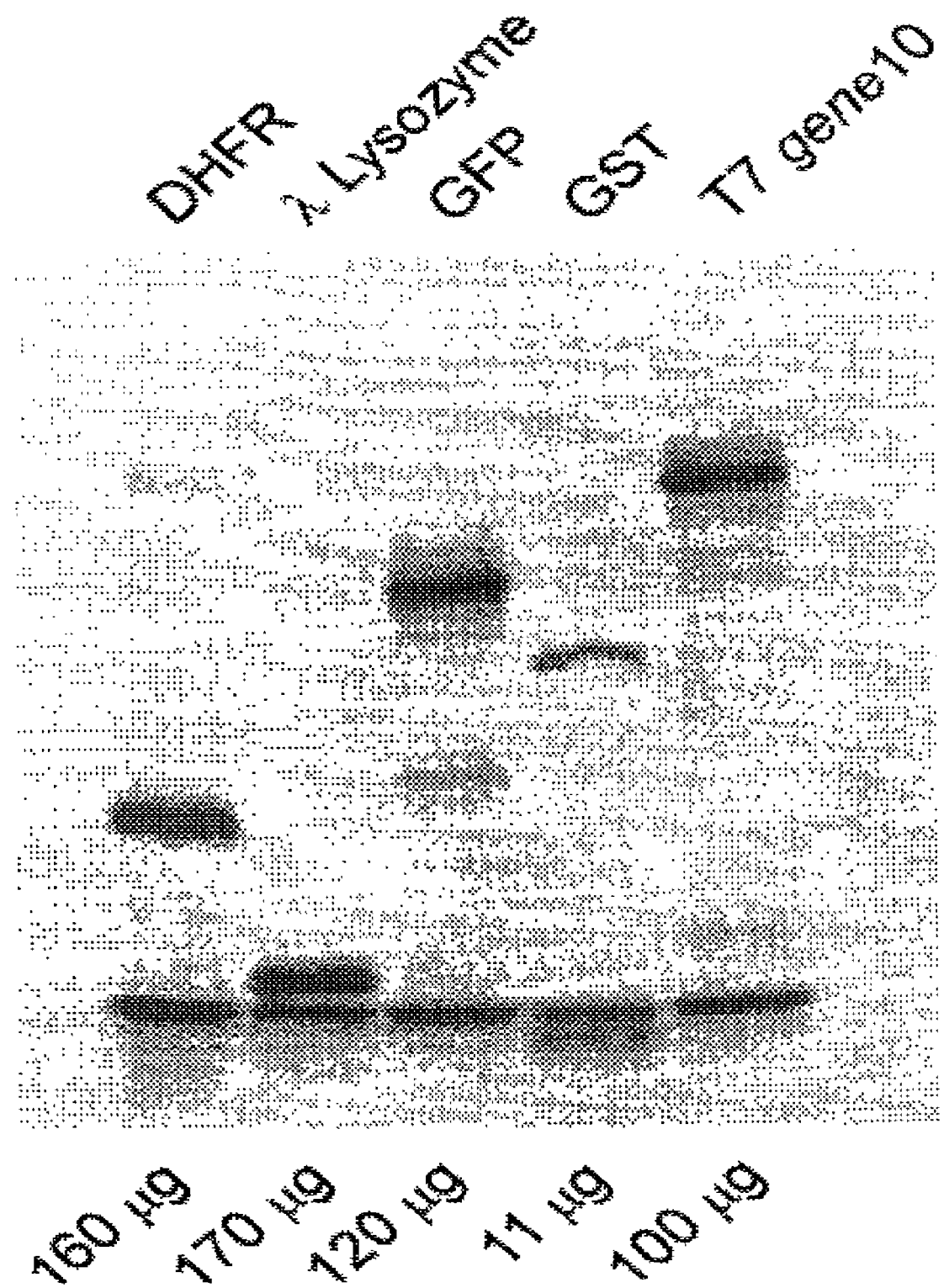
FIG. 13 shows SDS-PAGE patterns of various proteins synthesized by using the in vitro synthesis system of the present invention.

After confirming the activities of the His-tagged constituents of the reaction system, an in vitro protein synthesis system was constructed as in Example 14 with the use of His-tagged T7RNA polymerase. Using this synthesis system, full-length polypeptides of E. coli DHFR, λ-lysozyme, green fluorescent protein (GFP), glutathione transferase (GST) and T7 gene 10 protein were synthesized and the yield of each product was measured. FIG. 13 shows the results. Thus, it has been clarified that the synthesis system according to the present invention contains all of the components required in translation.

EXAMPLE 16

Poly(U)-poly(Phe) Synthesis

Poly(U)-poly(Phe) was synthesized in an in vitro reaction system as follows. Each reaction mixture comprised polymix buffer containing 1 mM of ATP, 1 mM of GTP, 10 mM of creatine phosphate, $2.8A_{260}$ units of tRNAmix, 1 mM of [$^{14}$C] labeled phenylalanine, and a factor mix. The factor mix contained 12 pmol of ribosome, 1 μg of EF-G*, 2 μg of EF-Tu*, 1 μg of EF-Ts*, 60 units of PheRS*, 0.2 μg of creatine kinase (CK), 0.15 μg of myokinase (MK) and 0.054 μg of nucleotide diphosphate kinase* (NDK*). Among the factors and enzymes, those marked "*" mean His-tagged ones. Reaction mixtures were incubated at 37° C. for 5 min, then 5 μg of poly (U) was added and reaction was started. Poly(Phe) was sampled in 8 μl aliquots with the passage of time and precipitated on 3MM filters with 10% trichloroacetic acid. Aminoacyl-tRNAs were deacylated at 85° C. and washed with 10% trichloroacetic acid followed by the measurement of radioactivity. Thus, the formation of the target product was confirmed.

Figure 7:
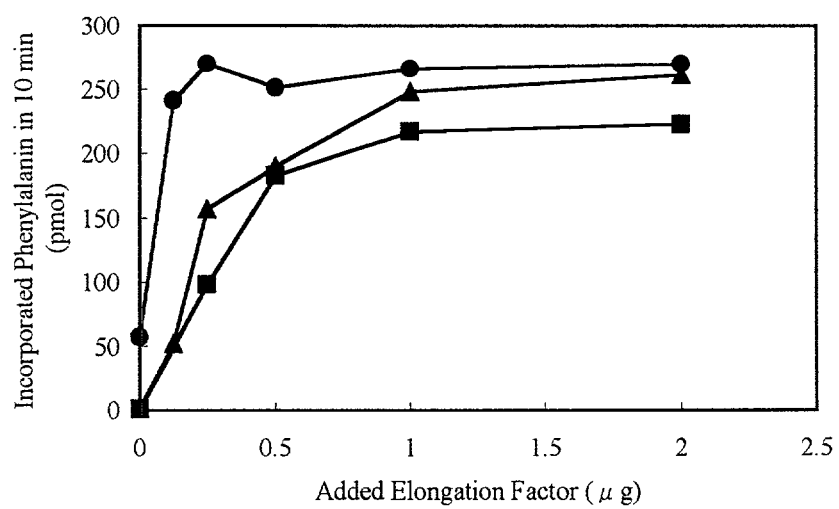
FIG. 7A shows the optimum concentrations of His-tagged termination factors in the in vitro poly(Phe) synthesis system according to the present invention expressed in the Phe incorporation levels.
FIG. 7B shows the progress of poly (Phe) synthesis reactions (expressed in the Phe incorporation levels) in the in vitro synthesis system according to the present invention and in the S100 extract system.
Figure 7:
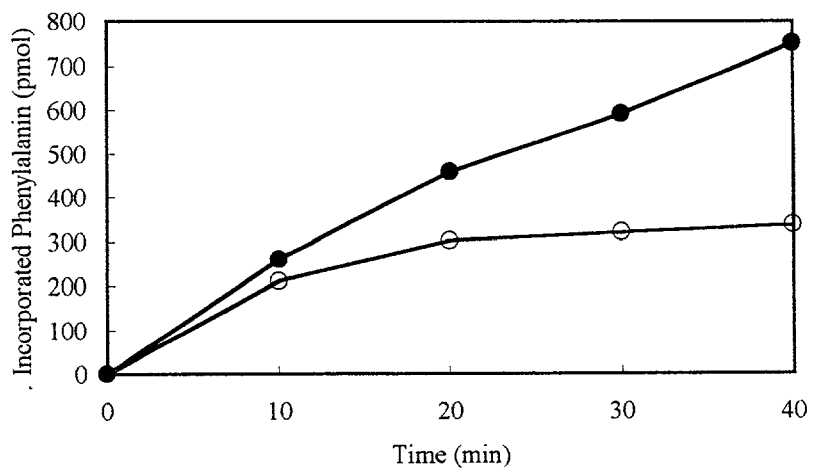

In the translation reactions as described above, the optimum concentrations of EF-G*, EF-Tu* and EF-Ts* were determined by examining the poly(Phe) yield in the in vitro reaction system under constant conditions but varying the concentration of each elongation factor. FIG. 7(A) shows the results thus obtained. In FIG. 7(A), ●, ▲ and ■ show the data of EF-G*, EF-Tu* and EF-Ts*, respectively.

Further, the data of the poly(Phe) synthesis in the above-described reaction system according to the present invention were compared with the data in the translation system with the use of the S100 extract. FIG. 7(B) shows the result. Although the reaction stopped after 20 min in the latter system (○), the reaction proceeded even after 40 min in the system of the present invention (●).

EXAMPLE 17

Activities of Termination Factors and Ribosome Recycling Factor

Activities of termination factors (RF1*, RF3* and RRF*; "*" manes "His-tagged") were measured according to Pavrov et al. (8) with slight modification. Reaction mixture (50 μl) were prepared based on the polymix buffer used in the translation experiment. Each reaction mixture comprised 1 mM of ATP, 1 mM of GTP, $2.8A_{260}$ units of tRNA mix, 1 mM of phenylalanine and leucine, 50 pmol of formylmethionyl-tRNA prepared by using [$^{35}$S] radioactive methionine and a His-tagged factor and enzyme mix (described hereinafter) . The factor and enzyme mix comprised 12 pml of ribosome, 1 μg of IF1*, 2 μg of IF2*, 0, 75 μg of IF3*, 1 μg of EF-G*, 2 μg of EF-Tu*, 1 μg of EF-Ts*, 0.5 μg of RF1*, 0.5 μg of RF3*, 0.5 g of RRF*, 50 units of PheRS* and 300 units of LeuRS*. RF1*, RF3* and RRF* were each removed from this factor and enzyme mix depending on the purpose to give respective reaction mixtures. Each reaction mixture was pre-incubated at 37° C. for 5min, and then 1 μg of MFL mRNA was added to initiate the translation. The reaction mixture was sampled in 5 μl aliquots with the passage of time and each sample was added to the same volume of 1 N HCl to cease the reaction. Further, 200 μl of ethyl acetate was added to elute the tripeptide (fMFL) and the radioactivity was measured with a liquid scintillation counter.

Figure 4:
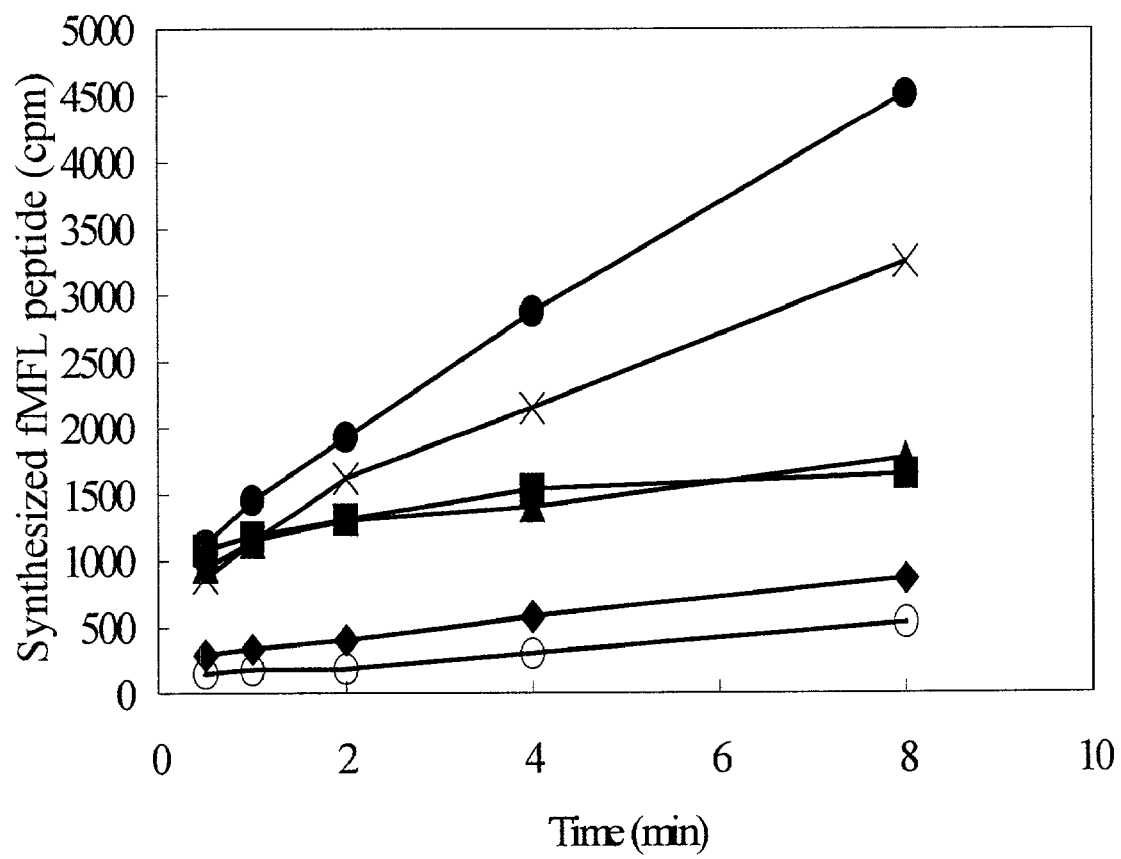
FIG. 4 shows the activities of His-tagged termination factors expressed in the yields of fMFL.

The activities of the termination factors RF1*, RF3* and RRF* were measured by using an in vitro translation system for synthetic mRNA encoding fMet-Phe-Leu-Stop (fMFL) . Namely, fMFL mRNA was translated in a system containing RF1*, RF3* and RRF* as termination factors (●), a system containing RF1* and RRF* (·), a system containing RF1* and RF3* (▲), a system containing RF1* alone (■), a system containing RF3* and RRF* (○) and a system free from any termination factor* (RRF* too) (◆) and the yields were measured. FIG. 4 shows the results. In FIG. 4, the peptide synthesized in the first cycle corresponds to about 1000 cpm on the y-axis. The system containing RF1*, RF3* and RRF* (●) shows a linear increase in the fMFL yield with the passage of time, which indicates that RF1*, RF3* and RRF* have the activities compared with other systems. In the system lacking RF1* (○), no peptide synthesis occurred. In the systems lacking RRF* (▲■◆), no ribosome recycling occurred.

EXAMPLE 18

DHFR Synthesis

Figure 8:
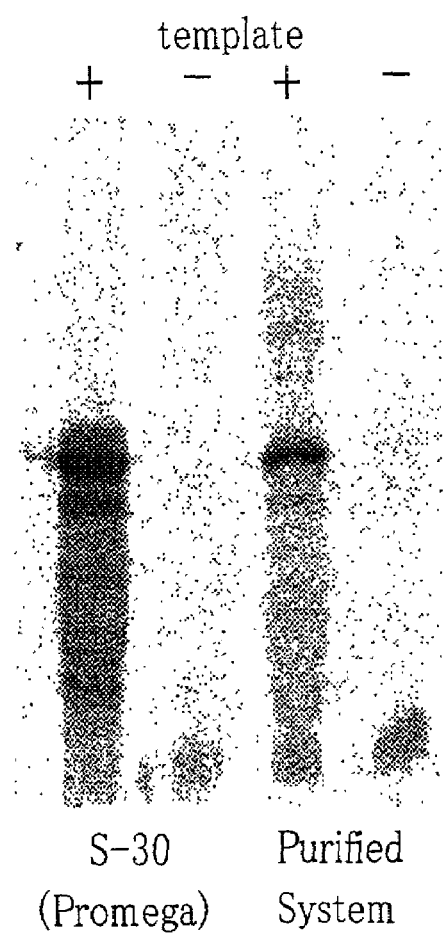
FIG. 8A shows 12% SDS-PAGE patterns of [$^{35}$S]Met-containing DHFR products, which were synthesized respectively by using the in vitro synthesis system according to the present invention and the S30 system.
FIG. 8B shows the DHFR activities of these products.
Figure 8:
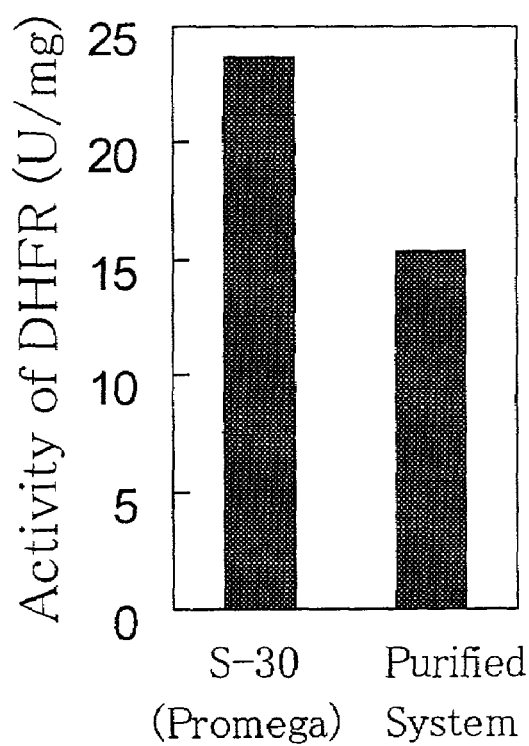

DHFR containing [$^{35}$S] methionine was synthesized by using the in vitro translation system according to the present invention and another translation system with the use of the S30 system(Promega). Each product was separated by 12% SDS-PAGE (sodium dodecyl suflate polyacrylamide gel electrophoresis) and detected by a BAS-1000 system (Fuji Film) followed by the measurement of the radioactivity. FIG. 8(A) shows the results of the separation by SDS-PAGE.

On the other hand, the activity of DHFR was measured as follows. In a reaction mixture containing 50 mM potassium phosphate buffer (pH7.0), 50 μM of DHF (dihydrofolic acid) and 60 μM of NADPH (reduced nicotinamide adenine dinucleotide phosphate), DHFR was synthesized at 30° C. and the decrease in $A_{340}$ was measured every 1 min. FIG. 8(b) shows the results.

Figure 9:
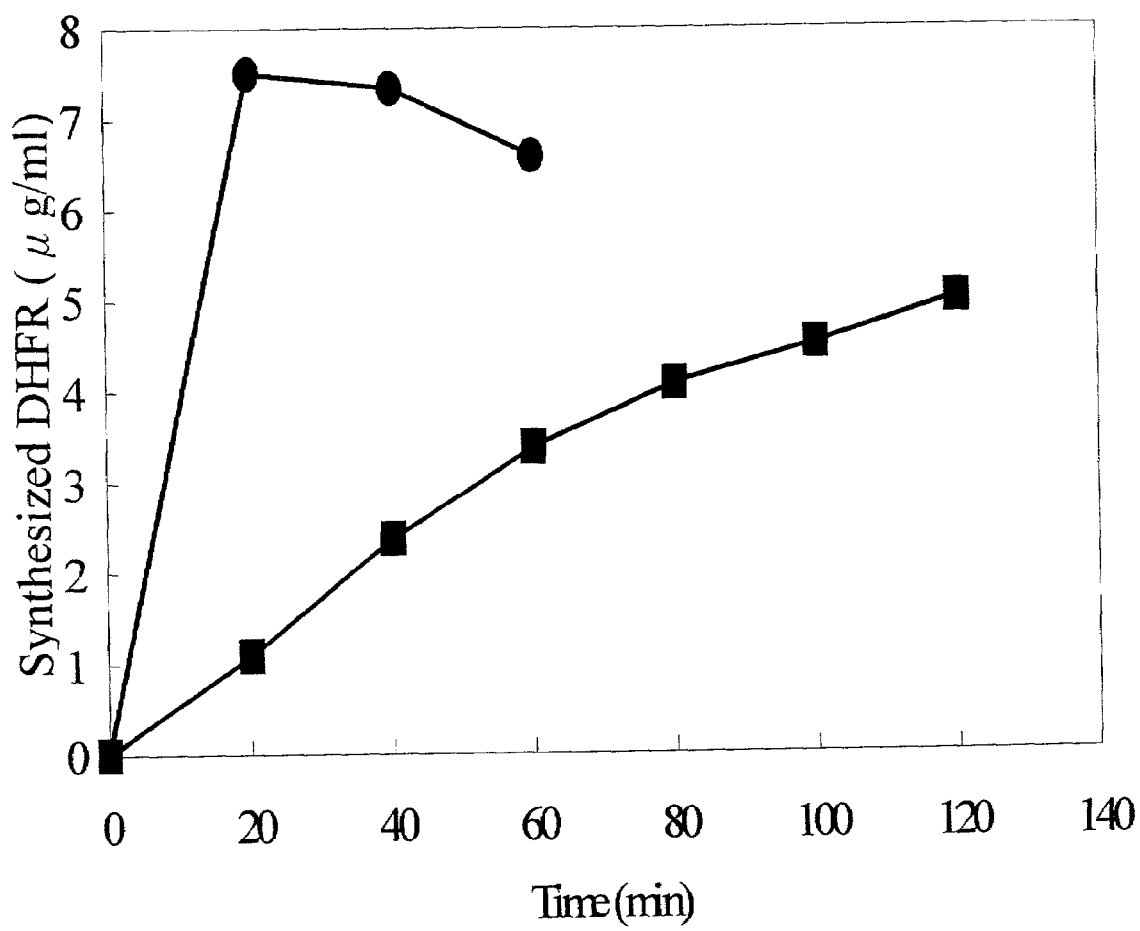
FIG. 9 shows the time courses of the DHFR synthesis reactions in the in vitro synthesis system of the present invention and in the S30 system.

FIG. 9 shows the reaction processes in the in vitro translation system according to the present invention and the S-30 system. In the in vitro translation system of the present invention (■), the reaction proceeded even after 120 minutes, while the DHFR yield attained the peak after 20 minutes in the S-30 system (●).

Figure 10:
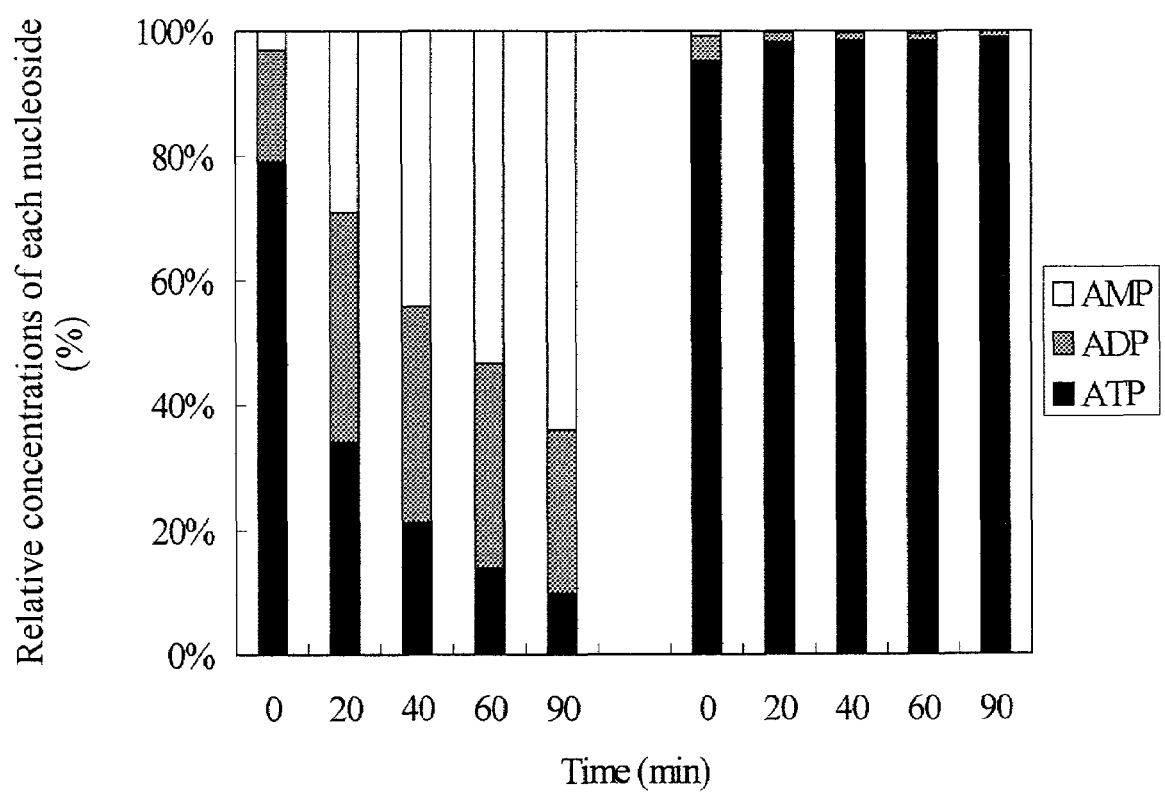
FIG. 10 shows the consumption of the energy source in the in vitro synthesis system of the present invention (right) and in the S30 system (left) with the passage of time.

To examine energy consumption, nucleoside triphosphate was hydrolyzed in the in vitro translation system according to the present invention and in the S-30 system. The hydrolysis in each system was monitored in the following manner while comparing the data. Using DHFR templates, translation was carried out in reaction mixtures containing [α-$^{32}$P] ATP or GTP at 37° C. Each reaction mixture was sampled in 2 µl aliquots with the passage of time and each sample was added to 150 µl of 10% formic acid. Then the mixtures were spotted on a polyethyleneimine TLC plate and the reaction products were developed with the use of 0.75M of potassium phosphate buffer (pH 3.75). After air-drying, the TLC plate was covered with a plastic wrap and autoradiographed. FIG. 10 shows the results wherein the data of the S-30 system are given left while the data of the invention system are given right. In the S-30 system, ATP was decreased with the passage of time, while the amount of ATP was maintained at an almost constant level in the system according to the present invention.

Figure 14:
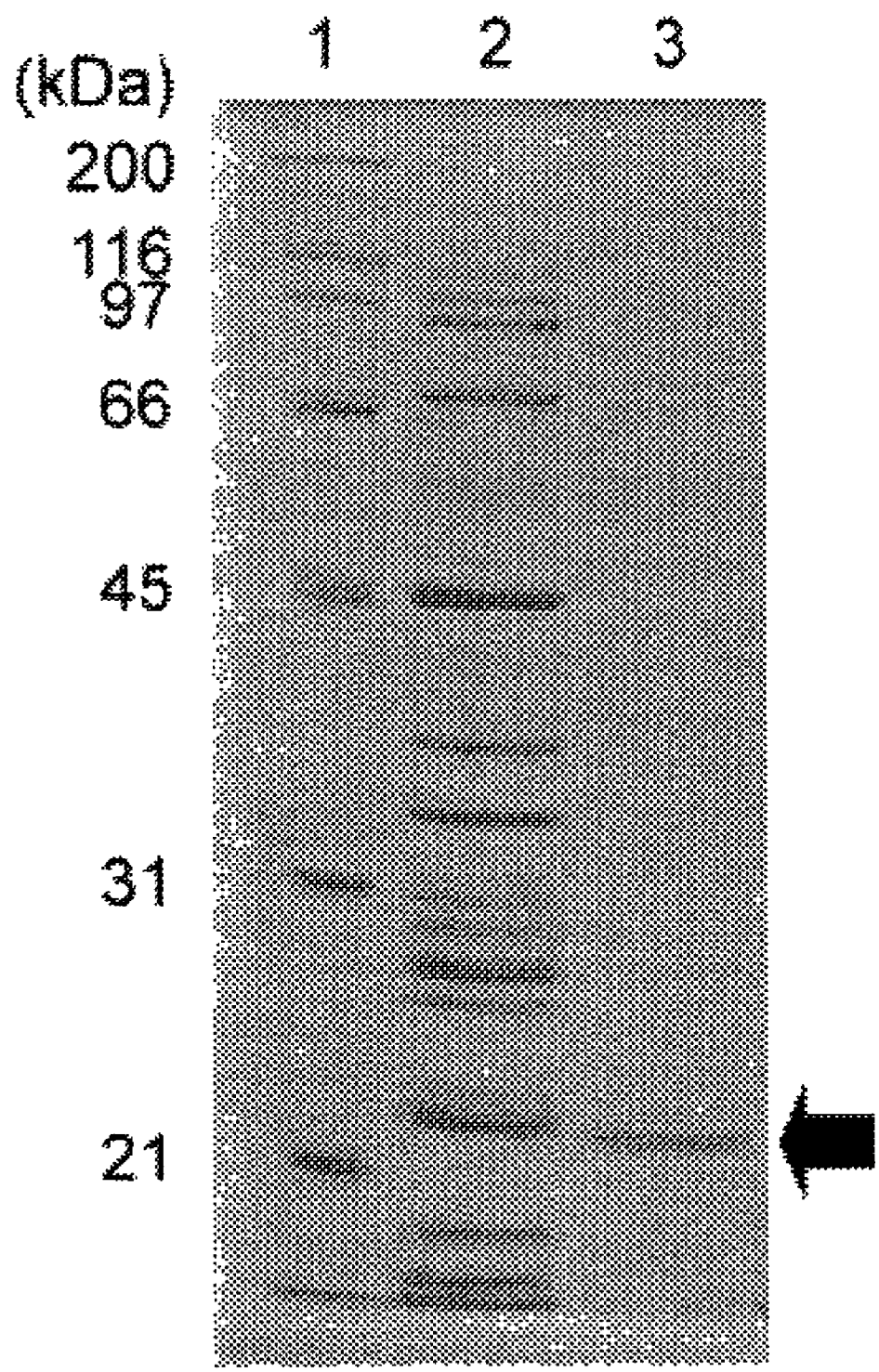
FIG. 14 shows the purity of DHFR, which is the translation product in the in vitro synthesis system of the present invention, after passing through ultra filtration membrane with cut-off of 100 kDa and a nickel column. In this figure, the arrow shows the position of DHFR.

To purify the DHFR synthesized, ribosome was eliminated by using an ultrafiltration membrane with a cut-off of 100 kDa. Next, all of the His-tagged components constituting the reaction system were eliminated by passing the reaction mixture through a nickel column. The reaction mixture before passing through the nickel column and the product obtained after passing through the nickel column were developed by 12% SDS-PAGE and stained with coomassie blue. FIG. 14 shows the results wherein lane 1 stands for the markers, lane 2 stands for the reaction mixture and lane 3 stands for the products (DHFR), indicating that the product was obtained as a single band.

EXAMPLE 19

Valine Residue Incorporation by Valyl Suppressor tRNA (Model of Incorporation of Unnatural Amino Acid)

In the in vitro translation system according to the present invention containing RF2* ("*" means "His-tagged") as a substitute for RF1* as a termination factor, a DHFR template, in which Asn at the 37-position (ATA codon) had been converted into UAG codon, was translated by using a chemically synthesized valyl suppressor tRNA. As a result, a truncated protein terminating at the 37-residue was synthesized in the sample containing RF1* (FIG. 11, lane 2), while a faint band assignable to this truncated protein was observed in the RF1*-free system (containing no RF2) (FIG. 11, lane 3). By incorporating RF2* thereinto, a protein product was observed at the same position (FIG. 11, lane 4) as normal DHFR (FIG. 11, lane 1). Based on these results, it was confirmed that the valine residue attached to suppressor tRNA had been incorporated into the 37-position of DHFR.

Effects of the Invention

By labeling protein components constituting a reaction system, individual protein components constituting the reaction system can be surely purified and thus a reaction system contaminated with no unknown component can be established. Moreover, it becomes possible thereby to easily isolate a target protein thus synthesized at a high purity.

Although it has been pointed out that lipopolysaccharides (LPSs) contained in cells and cell extracts exert various undesirable effects as endotoxins on living body, there is a technical problem that these LPSs can be hardly separated from target peptide products. However, this problem can be solved by using the in vitro peptide synthesis system according to the present invention.

Owing to the establishment of a reaction system free from any unknown components, a reaction can be continued over a long time, for example, 2 hr or longer even in a batch system. Furthermore, it is regarded as theoretically possible to increase the volume of a reaction mixture.

Using a flow system, the reaction can be continued for a longer time, which enables the practical production and purification of a protein in an in vitro reaction system. That is to say, this process makes it possible to economically supply certain enzymes which have been hesitantly applied to medical treatments because of high cost. As a result, the application range of medical treatments with the administration of enzymes, which are employed as a substitute for at least a part of gene therapy suffering from a technical problem in delivery, can be broadened.

According to the present invention, a system containing termination factors and a termination factor-free system can be definitely established and thus ribosome displays can be easily and selectively produced. Furthermore, it becomes possible to more accurately incorporate unnatural amino acid residues to desired positions.

Conventional cell-free protein synthesis systems with the use of prokaryotic cell extract suffer from a problem that the stability of an mRNA is seriously lowered when transcription and translation are not carried out simultaneously. In contrast, a reaction of translating an mRNA can stably proceed in the reaction system of the present invention.

After the completion of genome analyses, the mainstream of molecular biological studies is now switching over to gene analyses. Under these circumstances, the reaction system of the present invention, which quickens gene expression and identification of protein products and thus facilitates examination of gene functions, considerably contributes to advances in scientific technology.

Reference

1) Crowe, J., Dobeli, H., Gentz, R., Hochuli, E., Stuber, D., and Henco, K. (1994). 6×His-Ni-NTA chromatography as a superior technique in recombinant protein expression/purification. Methods Mol Biol 31, 371–87.

2) Hochuli, E., Dobeli, H., and Schacher, A. (1987). New metal chelate adsorbent selective for proteins and peptides containing neighbouring histidine residues. J Chromatogr 411, 177–84.

3) Smith, D. B., and Johnson, K. S. (1988). Single-step purification of polypeptides expressed in *Escherichia coli* as fusions with glutathione S-transferase. Gene 67, 31–40.

What is claimed is:

1. In a process for producing a peptide or a peptide derivative by using a reaction system of transcribing a DNA into an RNA and then translating the RNA produced or a reaction system of translating an RNA in vitro, wherein the improvement is all protein components of the reaction system are labeled with a fist substance which adheres to a second substance, and said second substance is used as an adsorbent for capturing said labeled protein components after translation of the peptide or peptide derivative to allow the separation of the produced peptide or a peptide derivative from the labeled protein components constituting the reaction system.

2. The process for producing a peptide or a peptide derivative as claimed in claim 1, wherein a plural number of combinations of said first and second substances are used in the process.

3. The process for producing a peptide or a peptide derivative as claimed in claim 1, wherein said protein components labeled with the first substance are protein factors and enzymes for the transcription or translation reaction.

4. The process for producing a peptide or a peptide derivative as claimed in claim 3, wherein said protein factors and enzymes for the transcription or translation reaction are selected from the group consisting of initiation factors, elongation factors, termination factors, aminoacyl-tRNA synthetase, methionyl-tRNA transformylase, RNA polymerase.

5. The process for producing a peptide or a peptide derivative as claimed in claim 1, wherein the protein components labeled with the first substances are the protein factors and enzymes for the transcription or translation reaction and other enzymes required in the constitution of the reaction system.

6. The process for producing a peptide or a peptide derivative as claimed in claim 5, wherein said other enzymes required in the constitution of the reaction system are selected from the group consisting of enzymes for regenerating energy in the reaction system and enzymes for hydrolyzing inorganic pyrophosphoric acid formed during the transcription or translation reaction.

7. The process for producing a peptide or a peptide derivative as claimed in claim 1, wherein the reaction system for transcribing a DNA into an RNA and then translating the RNA produced or the reaction system translating an RNA in vitro is free from termination factors.

8. The process for producing a peptide or a peptide derivative as claimed in claim 1, wherein a pair of said first and second substances adhering to each other are substances mutually interacting in affinity chromatography.

9. The process for producing a peptide or a peptide derivative as claimed in claim 8, wherein the combination of said first and second substances mutually interacting in affinity chromatography is selected from among combinations of substances capable of forming a bond between a protein or a peptide fragment and a metal ion, a bond between an antigen and an antibody, a bond between a protein and a protein or a peptide fragment, a bond between a protein and a specific low-molecular weight compound selected from the group consisting of amino acids, DNAs, dyes, vitamins and lectins, a bond between a protein and a saccharide, or a bond between a protein or a peptide fragment and an ion exchange resin.

10. The process for producing a peptide or a peptide derivative as claimed in claim 9, wherein said combination of first and second substances forming a bond between a protein or a peptide fragment and a metal ion is a histidine tag and a nickel complex or a cobalt complex.

11. The process for producing a peptide or a peptide derivative as claimed in claim 1, wherein said combination of first and second substances is selected from the substances magnetically adhering to each other.

12. A kit of protein components for a reaction system for producing a peptide or a peptide derivative by transcribing DNA into RNA and then translating the RNA produced or translating RNA in vitro wherein the kit comprises all protein components of the system which are labeled with a first substance which adheres to a second substance which is used as an adsorbent for capturing said labeled protein components after translating and that said protein component is selected from the group consisting of enzymes and protein factors constituting the reaction system.

13. The kit of protein components as claimed in claim 12, wherein said protein components are selected from the protein factors and enzymes for the transcription or translation reaction and other enzymes required in the constitution of the reaction system.

14. The kit of protein components as claimed in claim 13, wherein said protein factors and enzymes for the transcription or translation reaction are selected from the group consisting of initiation factors, elongation factors, termination factors, aminoacyl-tRNA synthetase, methionyl-tRNA transformylase and RNA polymerase.

15. The kit of protein components as claimed in claim 13, wherein said enzymes required in the constitution of the reaction system other than the protein factors and enzymes for the transcription or translation reaction are selected from the group consisting of enzymes for regenerating energy in the reaction system and enzymes for hydrolyzing inorganic pyrophosphoric acid formed during the transcription or translation reaction.

16. The kit of protein components as claimed in claim 12 which comprises an adsorbent as said second substance for capturing the protein components labeled with said first substance.

17. The kit of protein components as claimed in claim 12 which comprises a plural number of combinations of said first substance with said second substance.

* * * * *